US008218132B2

(12) United States Patent
Yamada et al.

(10) Patent No.: US 8,218,132 B2
(45) Date of Patent: Jul. 10, 2012

(54) PARTICLE MEASURING DEVICE AND PARTICLE SIZE MEASURE DEVICE

(75) Inventors: Yukio Yamada, Tokyo (JP); Shinpei Okawa, Tokyo (JP); Taisuke Hirono, Tokyo (JP)

(73) Assignees: The University of Electro-Communications, Tokyo (JP); Kowa Company, Ltd., Aichi (JP)

( * ) Notice: Subject to any disclaimer, the term of this patent is extended or adjusted under 35 U.S.C. 154(b) by 504 days.

(21) Appl. No.: 12/595,348

(22) PCT Filed: Apr. 8, 2008

(86) PCT No.: PCT/JP2008/056939
§ 371 (c)(1),
(2), (4) Date: Oct. 9, 2009

(87) PCT Pub. No.: WO2008/132995
PCT Pub. Date: Nov. 6, 2008

(65) Prior Publication Data
US 2010/0110177 A1 May 6, 2010

(30) Foreign Application Priority Data

Apr. 12, 2007 (JP) ................................. 2007-104901
Apr. 12, 2007 (JP) ................................. 2007-104931

(51) Int. Cl.
*G01P 3/36* (2006.01)
(52) U.S. Cl. ................ 356/27; 356/26; 356/29; 356/32; 356/335; 250/573

(58) Field of Classification Search .................. 348/135; 356/27–29, 32, 303, 335; 250/573
See application file for complete search history.

(56) References Cited

U.S. PATENT DOCUMENTS
6,653,651 B1 * 11/2003 Meinhart et al. .............. 250/573

FOREIGN PATENT DOCUMENTS

| JP | 05-45274 | 2/1993 |
|----|----------|--------|
| JP | 06-043090 | 2/1994 |
| JP | 09-089753 | 9/1995 |
| JP | 2007-010524 | 1/2007 |

OTHER PUBLICATIONS

Particle sizing using imaging velocimetry for two-pase flows by Kadambi et al. Dec. 1, 1998 publication of Powder Technology; vol. 100, issues 2-3, pp. 251-259.*
Jun'ichiro Otaki, "Bisho Ryurochu o Nagareru Hakkekkyu Keisu Hoho no Kaihatsu", Spectroscopical Socity of Japan Koen Yoshishu, Nov. 8, 2006, Nen Shuki, pp. 124 to 125.
International Search Report from International Application No. PCT/JP2008/056939 dated Jul. 8, 2008, issued by Japanese Patent office.

* cited by examiner

*Primary Examiner* — Frantz Jean
(74) *Attorney, Agent, or Firm* — Duane Morris LLP

(57) ABSTRACT

Particles flowed through a micro-channel are imaged by imaging means. Particle speed measuring means determines the particle speed from the image data. Particle counting means counts the particles flowed for a predetermined time. Particle size measuring means measures the size of the particles. The measurements of the particles flowed at a predetermined timing are managed by data associating means. With this, the speed, number and size of particles flowed through a micro-channel can be determined at a time, and associated data can be obtained.

13 Claims, 25 Drawing Sheets

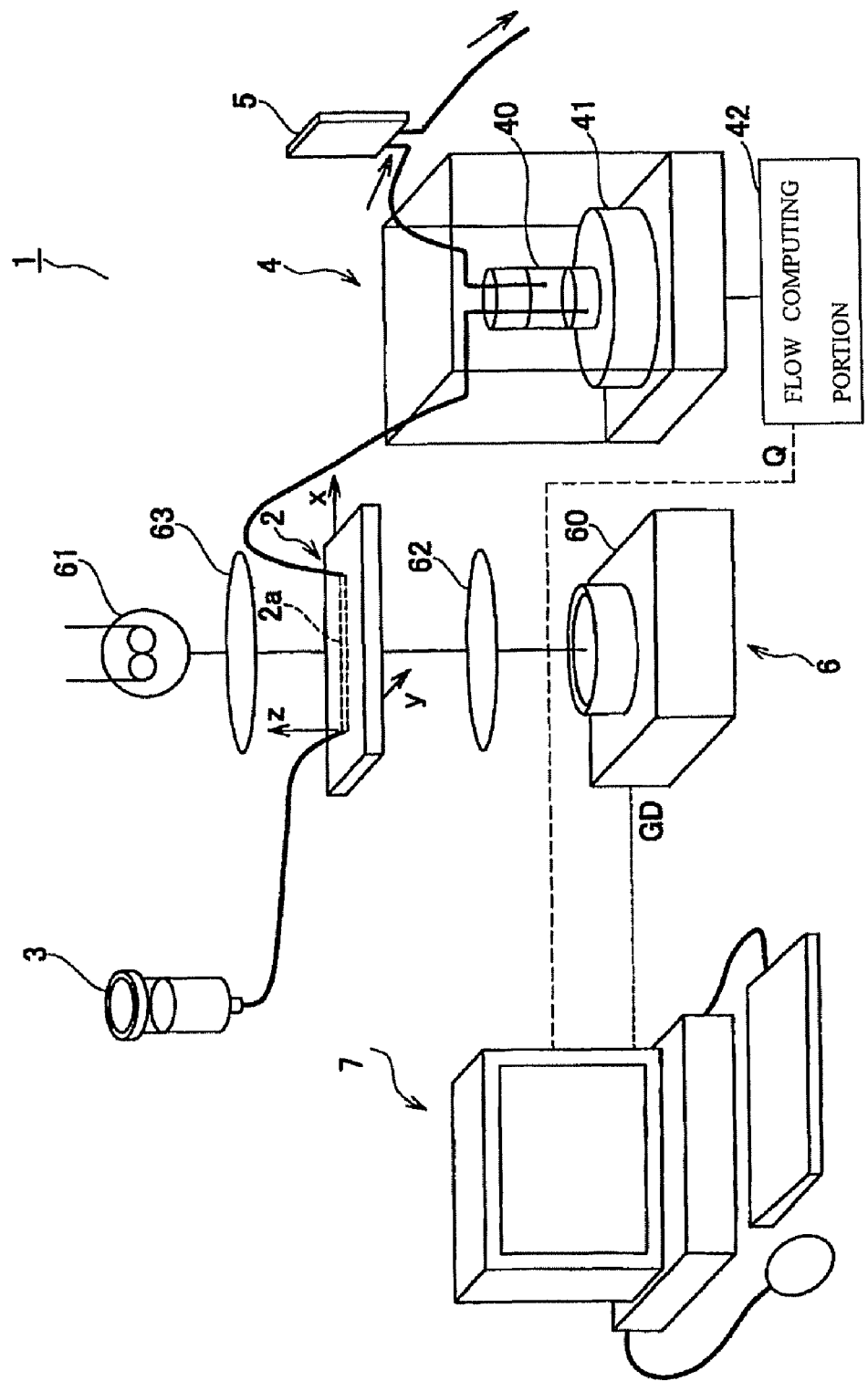

FIG. 3
(a)
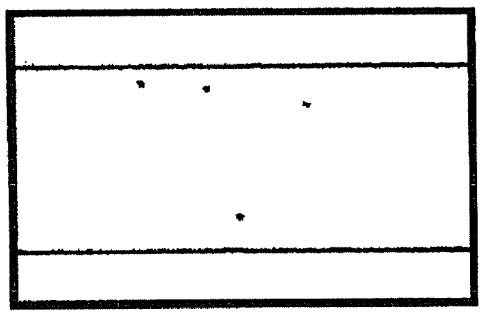
(b)
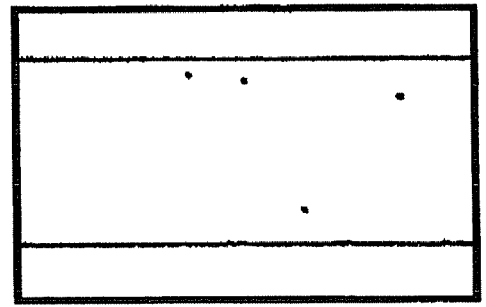
(c)
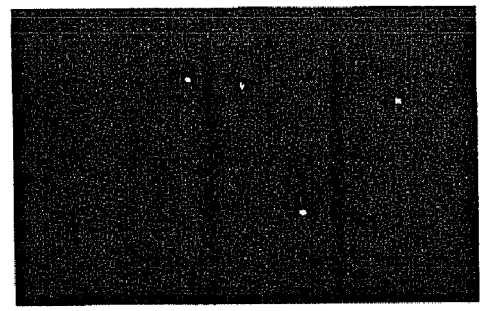

F I G. 7
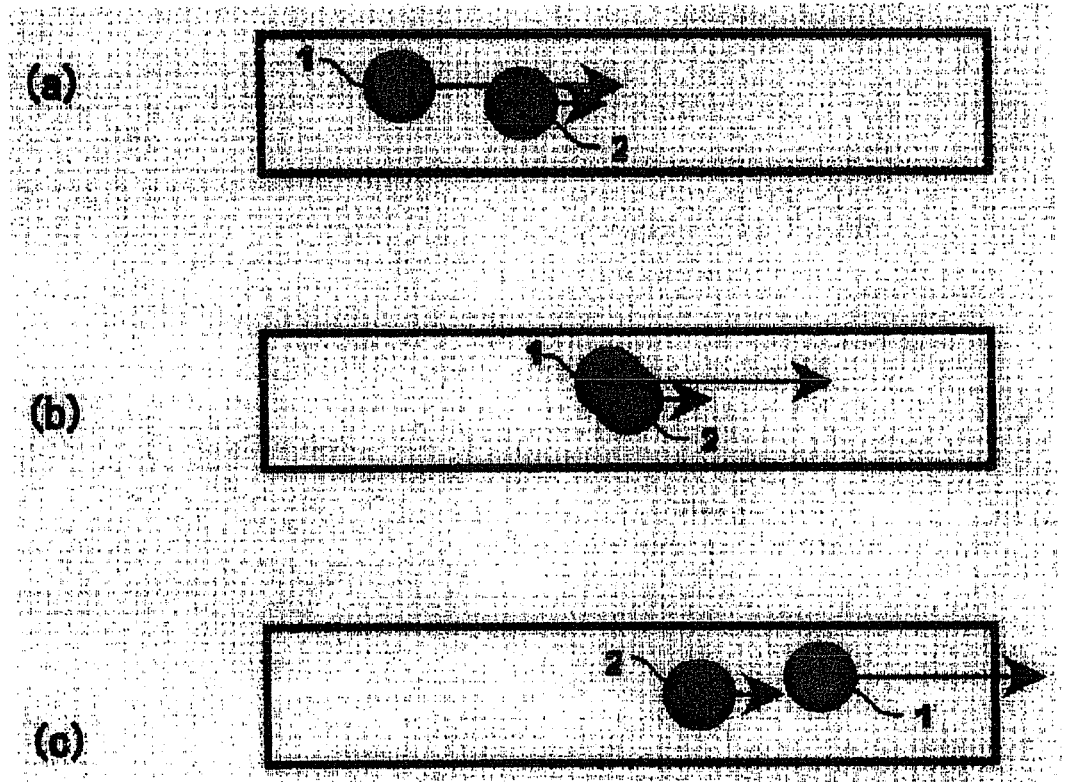

F I G. 8
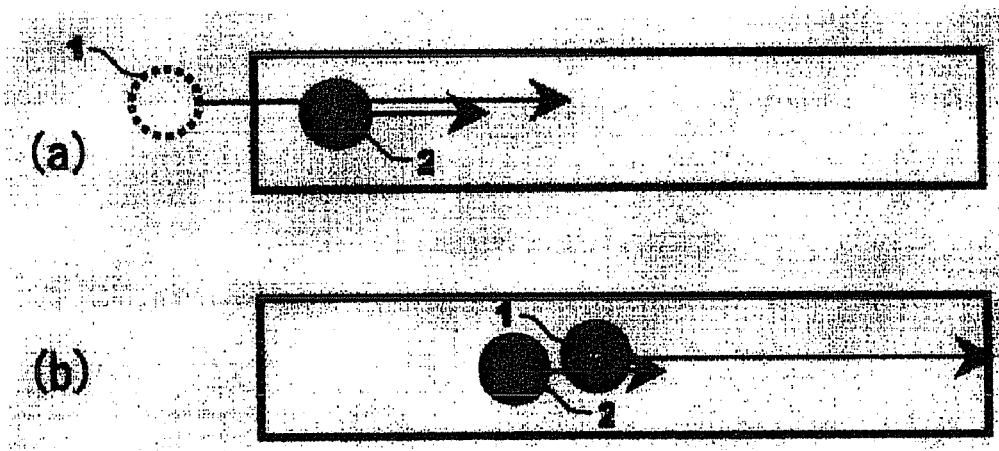

F I G. 9
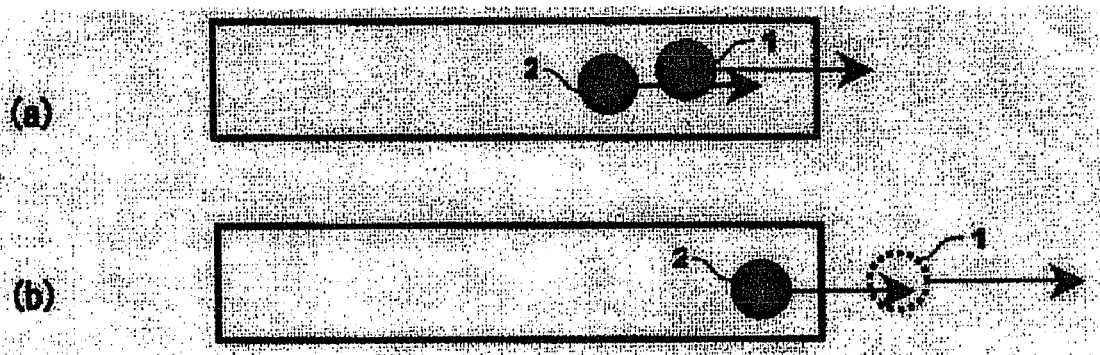

FIG. 12
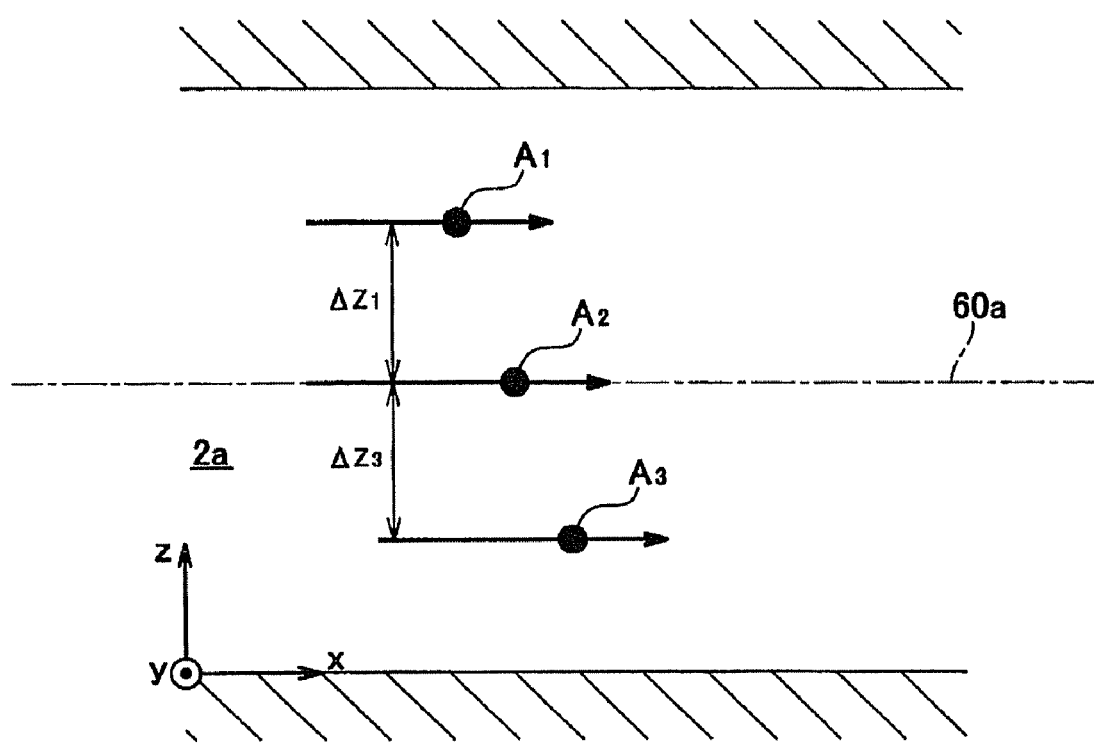
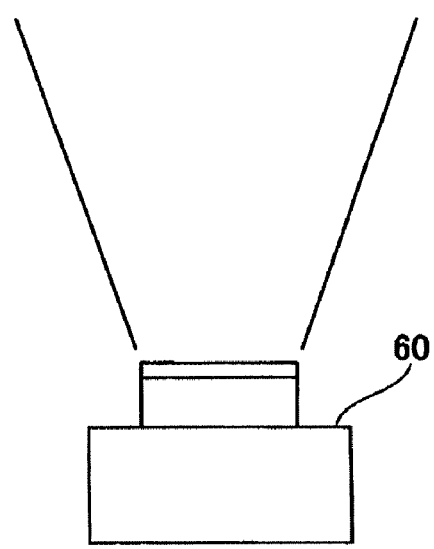

FIG. 19
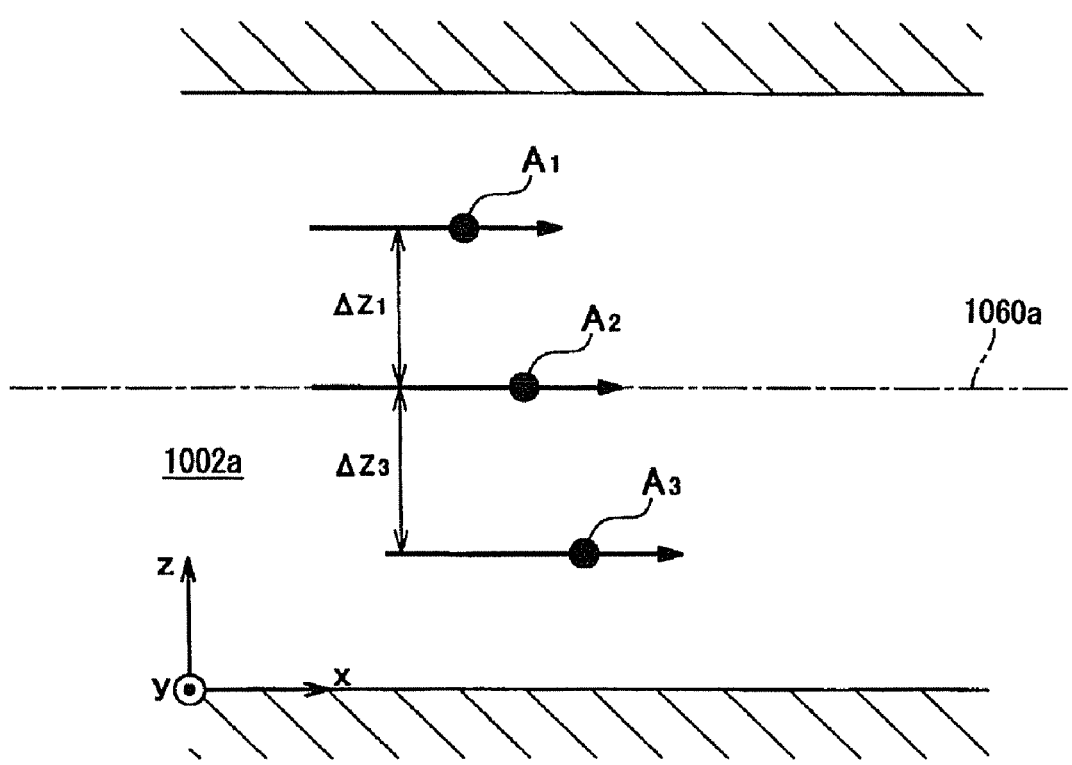
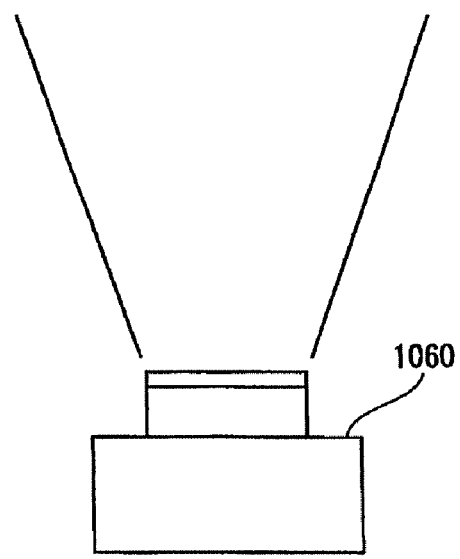

F I G. 2 2
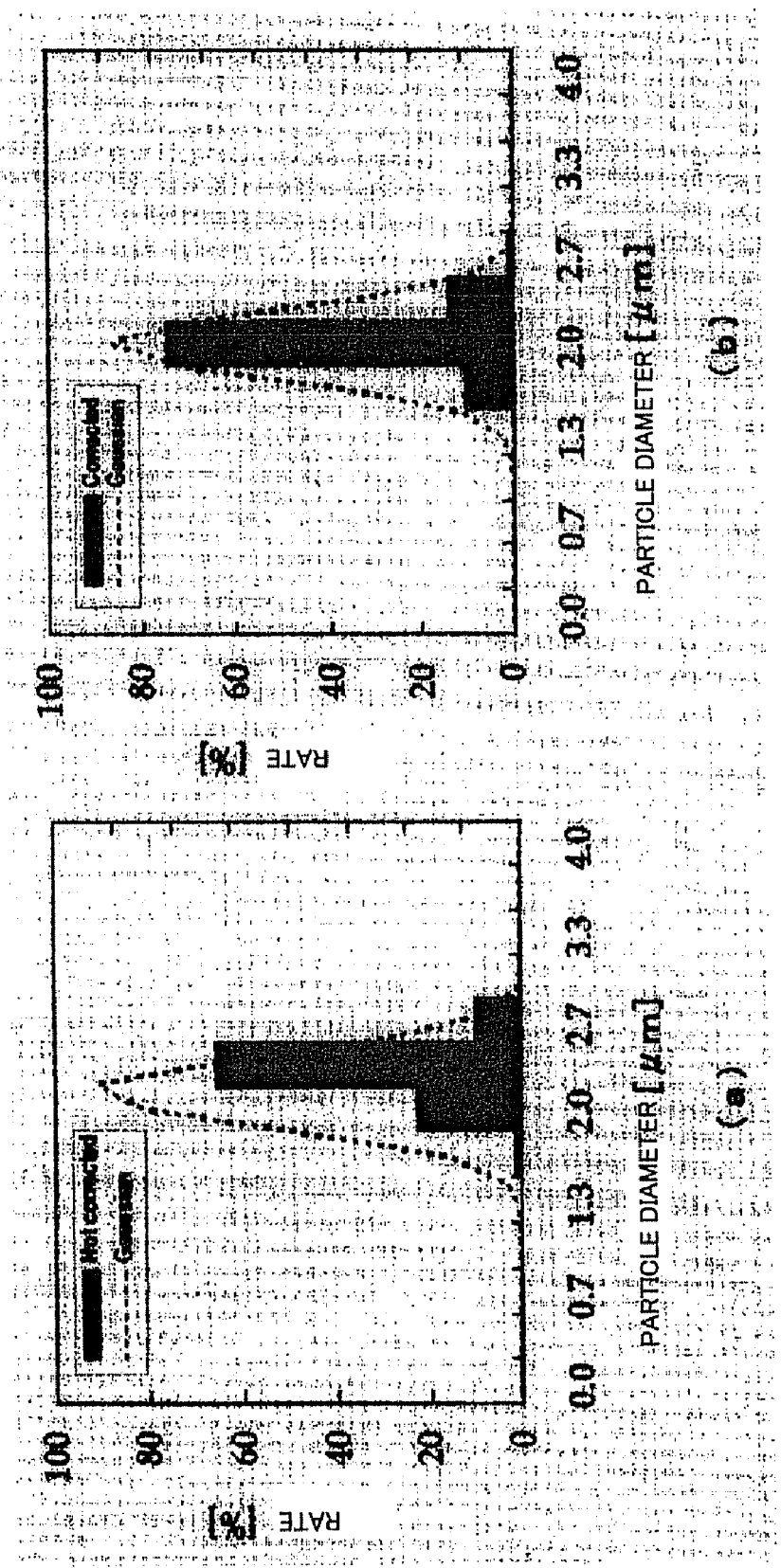

PARTICLE MEASURING DEVICE AND PARTICLE SIZE MEASURE DEVICE

CROSS-REFERENCE TO RELATED PATENT APPLICATIONS

The present application is a U.S. national stage application under 35 U.S.C. §371 of PCT Application No. PCT/JP2008/056939, filed Apr. 12, 2007, the entirety of which is incorporated herein by reference.

TECHNICAL FIELD

This invention relates to a particle measuring device for measuring particle speed, particle number and particle size of particles flowed. Besides, the invention relates to a particle size measuring device for measuring diameter of particles mixed in fluid.

BACKGROUND ART

A method of imaging particles flowed with fluid and analyzing particles from the image has been used in various kinds of fields. For example, this method is disclosed in Japanese patent application publication No. H08-136439.

DISCLOSURE OF INVENTION

Problems to be Solved

There are device for measuring particle speed, device for counting particle number, and device for measuring particle size as a conventional device for analyzing particles, but no effective device for simultaneously measuring the above-mentioned three has not yet been proposed.

It is inevitable for diagnosis of various kinds of diseases to know size or number of aggregation lumps formed due to aggregation ability of blood cells, such as platelets for correctly understand an aggregation reaction, and a platelet aggregometer for measuring an aggregation lump as a particle is known. But, a device for measuring the particle diameter, the number of particles and the like at the same time, not separately measuring these, is desired for diagnosis of diseases.

In other words, a particle measuring device for simultaneously measuring particle speed, particle number and particle diameter is desired to be developed.

On the other hand, a method of imaging fluid mixing particles therein and computing particle diameter through analyze of the image obtained has been known. See Japanese patent application publication No. H8-136439.

Such a device can be utilized in various kinds of art fields, and the device with a simple structure which measuring accuracy is high is desired.

That is, the particle size measuring device with a simple structure for obtaining particle diameter with high accuracy is desired.

Means for Solving Problems

The invention is a particle measuring device for measuring particles based upon image data, comprising:
a micro-channel wherein fluid mixing particles therein flows, forming laminar flow;
imaging means, for imaging said particles flowed in said micro-channel from a direction almost orthogonal to a fluid flow direction;
particle speed measuring means, for measuring speed of said particle flowed based upon said image data obtained by imaging through said imaging means;
particle number counting means, for counting number of said particles flowed within a predetermined time based upon said image data obtained by imaging through said imaging means;
particle size measuring means, for measuring diameter of said particle flowed based upon said image data obtained by imaging through said imaging means; and
data associating means, for associating measurement values measured by respective measuring means and time with each other based upon time when measuring through said respective measuring means and controlling thus associated.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced, and easier measurement is possible.

The invention is the particle measuring device, wherein said particle speed measuring means has
a movement distance computing portion, for computing movement distance of each particle by executing imaging processing on two or more stationary images obtained by imaging through said imaging means, and
a particle speed computing portion, for computing the speed by dividing said computed movement distance by imaging interval.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced, and easier measurement is possible.

The invention is the particle measuring device, wherein said particle number counting means has
a differential image forming portion, for forming a differential image from two stationary images obtained by imaging through said imaging means, and
a relating portion, for relating said particle to a position to which said particle moved; and
a particle number counting portion, for counting number of said particles based upon data from said relating portion.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced, and easier measurement is possible.

The invention is the particle measuring device, wherein said particle number counting means has
a particle position predicting portion, for predicting a position of said particle in a next stationary image from speed of said respective particles obtained through said particle speed measuring means;

a particle movement predicting portion, for predicting movement of said particle based upon data of said particle position predicting portion; and a particle number compensating portion, for compensating measurement data of said particle number counting portion based upon data from said particle movement predicting portion.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced, and easier measurement is possible. Besides, it is possible to correctly count the number of particles since such counting is executed, taking consideration of the movement of the particle.

The invention is the particle measuring device, wherein said particle size measuring means has a first particle size computing means, for computing a diameter of said particle on the image based upon said image data obtained by imaging through said imaging means.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced, and easier measurement is possible.

The invention is the particle measuring device, wherein said particle size measuring means has a particle size compensating portion, for compensating a computed result of said first particle size computing means based upon amount of deviation of said particle with respect to a focal face of said imaging means.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced, and easier measurement is possible. Besides, it is possible to correctly the diameter of the particle.

The invention is the particle measuring device, wherein said fluid is one of liquid, gas, two-phase fluid of liquid-gas, two-phase fluid of liquid-solid, two-phase fluid of gas-solid, and multi-phase fluid of liquid-gas-solid.

In such a case, number of the particles flowed in a predetermined time, and the speed of the particle and the diameter of the particle can be measured such that these three are associated with each other. Since the fluid flows, forming laminar flow, the flowing direction of each particle is constant, and it is possible to easily predict the movement of the particle through the relating portion thereby. According to this aspect of the invention, the computing volume can be widely reduced; and easier measurement is possible.

The invention is a particle size measuring device for measuring diameter of particles mixed in fluid, comprising:

a micro-channel for flowing fluid including particles therein in a first axial direction;

imaging means, for imaging said particles flowed in said micro channel, said imaging means being located so as to image a third axial direction almost orthogonal to said first axial direction;

flow measuring means, for measuring flow of fluid flowed in said micro-channel;

a first particle size computing means, for computing an apparent diameter of said particle on an image based upon image data obtained by imaging through said imaging means;

flow speed computing means, for computing flow speed of said particle based upon said image data;

second axis directional position measuring means, for measuring a position of said particle in a second axial direction almost orthogonal to said first axial direction and said third axial direction from said image data;

third axis directional position computing means, for computing a position of said particle in said third axial direction based upon computed results through said flow measuring means, said flow speed computing means and said second axis directional position measuring means and the Navier-Stokes equation regarding fluid flowed in said micro-channel;

deviation computing means, for computing amount of deviation of said particle in said third axial direction with respect to said focal face of said imaging means based upon computed result of said third axis directional position computing means;

blur predicting means, for predicting degree of blur of an image of said particle based upon computed result of said deviation computing means; and second particle size computing means, for compensating said apparent diameter of said particle based upon predicted result of said blur predicting means.

In such a case, it is possible to accurately measure the diameter of the particle with a simple structure.

The invention is a particle size measuring device for measuring diameter of particles mixed in fluid, comprising:

a micro-channel for flowing fluid including particles therein in a first axial direction;

imaging means, for imaging said particles flowed in said micro channel, said imaging means being located so as to image a third axial direction almost orthogonal to said first axial direction;

flow measuring means, for measuring flow of fluid flowed in said micro-channel;

a first particle size computing means, for computing apparent diameter of said particle on an image based upon image data obtained by imaging through said imaging means;

flow speed computing means, for computing flow speed of said particle based upon said image data;

a second axis directional position measuring means, for measuring a position of said particle in a second axial direction almost orthogonal to said first axial direction and said third axial direction from said image data;

third axis directional position computing means, for computing a position of said particle in said third axial direction based upon computed results through said flow measuring means, said flow speed computing means and said second axis directional position measuring means and the Navier-Stokes equation regarding fluid flowed in said micro-channel;

deviation computing means, for computing amount of deviation of said particle in said third axial direction with respect to said focal face of said imaging means based upon computed result of said third axis directional position computing means; and third particle size computing means, for computing particle diameter from said apparent diameter of said particle, said amount of deviation and the following expression.

$$f(d_p, d_e', \Delta z) = 0 \quad \text{[Expression 1]}$$

where $d_e'$=said apparent particle diameter $\Delta z$=said amount of deviation.

In such a case, it is possible to accurately measure the diameter of the particle with a simple structure.

In the particle size measuring device according to the invention, said expression is the following one.

$$d_e' = \sqrt{M^2 d_p^2 + d_s^2 + \left(\frac{MD_a \cdot \Delta z}{(s_o + \Delta z)}\right)^2} \quad \text{[Expression 2]}$$

where $d_e'$=said apparent particle diameter
M=magnification of said imaging means
$d_s$=airy disk diameter due to diffraction
$D_a$=effective diameter of lens
$s_o$=distance from main point of lens to focal face
$\Delta z$=said amount of deviation.

In such a case, it is possible to accurately measure the diameter of the particle with a simple structure.

The invention is the particle size measuring device, wherein said first particle size computing means is comprised of an area computing portion, for computing area of said particle based upon said image data, and a particle size computing portion, for computing said apparent particle diameter based upon said area computed by said area computing portion and the following expression.

$$d_e' = 2\sqrt{\frac{S}{\pi}} \quad \text{[Expression 3]}$$

In such a case, it is possible to accurately measure the diameter of the particle with a simple structure.

The invention is the particle size measuring device, wherein said micro-channel has a form so as to flow said fluid, forming laminar flow.

In such a case, it is possible to accurately measure the diameter of the particle with a simple structure.

The invention is the particle size measuring device, wherein said flow measuring means is comprised of a storage container for storing fluid flowed out of said micro-channel, a weight measuring portion for measuring weight of fluid stored in said storage container, and a flow computing portion for computing flow based upon a result measured by said weight measuring portion and time data.

In such a case, it is possible to accurately measure the diameter of the particle with a simple structure.

The invention is the particle size measuring device, further comprising fourth particle size computing means, for compensating errors due to a phenomenon of diffraction of light by executing deconvolution procedure.

In such a case, it is possible to accurately measure the diameter of the particle with a simple structure.

The invention is the particle size measuring device, wherein said fluid is one of liquid, gas, two-phase fluid of liquid-gas, two-phase fluid of liquid-solid, two-phase fluid of gas-solid, and multi-phase fluid of liquid-gas-solid.

In such a case, it is possible to accurately measure the diameter of the particle with a simple structure.

BRIEF DESCRIPTION OF DRAWINGS

FIG. 2 is a typical view showing the whole structure of the particle measuring device according to the invention;

FIG. 3(a), (b) are views showing two stationary images (photographs) obtained by imaging means, FIG. 3(c) is a view (photograph) of a differential image between both stationary images;

FIG. 7 is a typical view showing such a state that a particle catches up to the other particle and passes;

FIG. 8 is a typical view showing flowing forms of particles;

FIG. 9 is a typical view showing another flowing forms of particles;

FIG. 12 is a typical view of flowing of particles seen from a second axial direction;

FIG. 19 is a typical view showing flowing of particles which is seen from the second axial direction;

FIG. 22(a) is a view showing analysis result with no compensation through second particle size computing means, and FIG. 22(b) is a view showing analysis result with compensation through the second particle size computing means;

EXPLANATION OF REFERENCE NUMBERS

Figure 1:
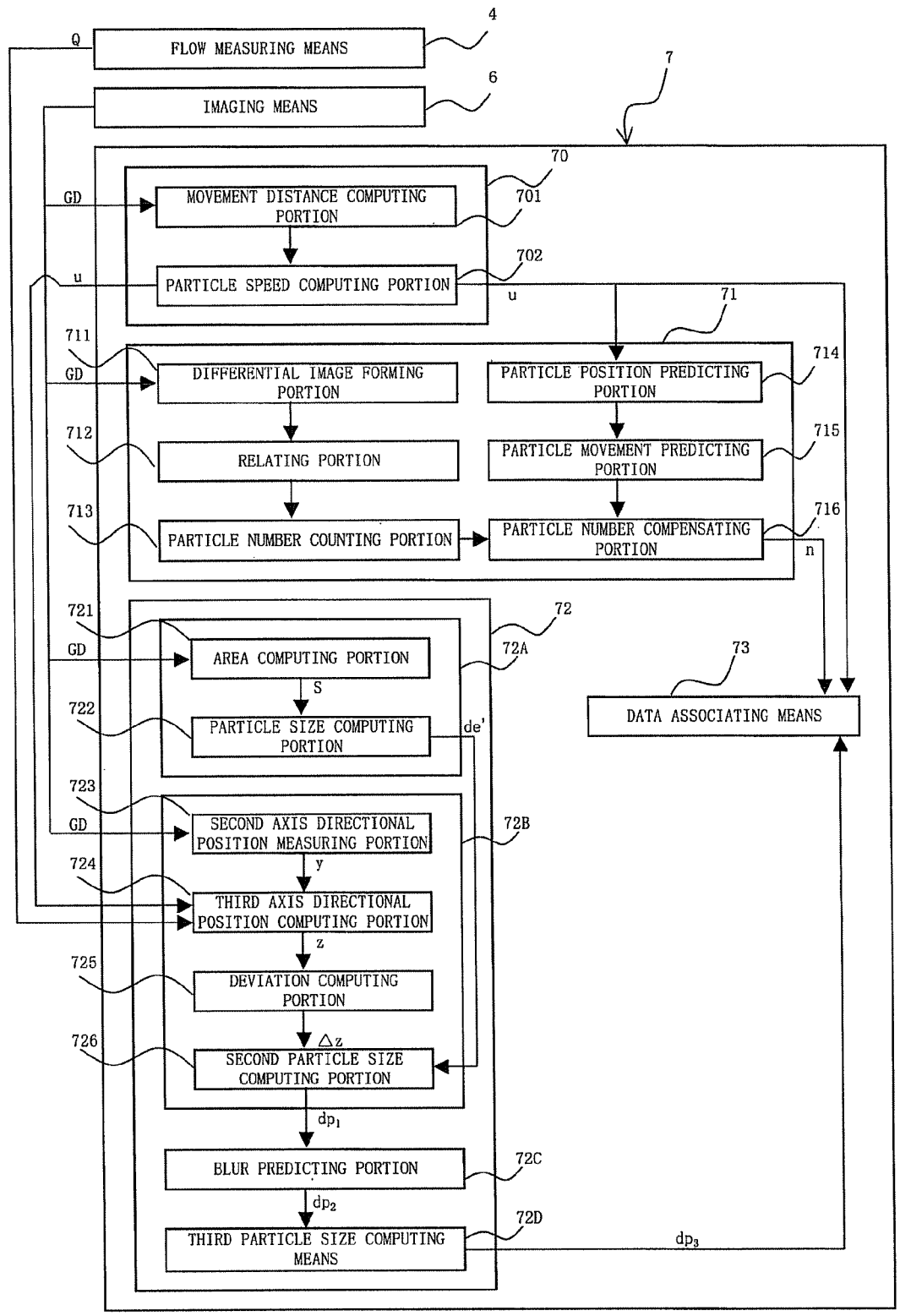
FIG. 1 is a block diagram showing an example of a structure of an important portion (data processor) of a particle measuring device according to the invention.

1 . . . particle measuring device
2a . . . micro-channel

6 . . . imaging means
70 . . . particle speed measuring means
71 . . . particle number counting means
72 . . . particle size measuring means
72A . . . first particle size computing means
72B . . . particle size compensating portion
73 . . . data associating means
701 . . . movement distance computing portion
702 . . . particle speed computing portion
711 . . . differential image forming portion
712 . . . relating portion
713 . . . particle number counting portion
714 . . . particle position predicting portion
715 . . . particle movement predicting portion
716 . . . particle number compensating portion
1001 . . . particle size measuring device
1002a . . . micro-channel
1004 . . . flow measuring means
1006 . . . imaging means
1060a . . . focal face
1070 . . . first particle size computing means
1071 . . . flow speed computing means
1072 . . . second axis directional position measuring means
1073 . . . third axis directional position measuring means
1074 . . . deviation computing means
1075 . . . blur predicting means
1076 . . . second particle size computing means
1077 . . . third particle size computing means
1701 . . . area computing portion
1702 . . . particle size computing portion
$d_e'$ . . . apparent particle diameter
$d_p$ . . . compensated particle diameter
GD . . . image data
u . . . flow speed
x . . . first axial direction
y . . . second axial direction
z . . . third axial direction
$\Delta z$ . . . amount of deviation

BEST MODE FOR CARRYING OUT THE INVENTION

Embodiments of the invention are now mentioned, referring to appended drawings.

First Embodiment

Figure 4:
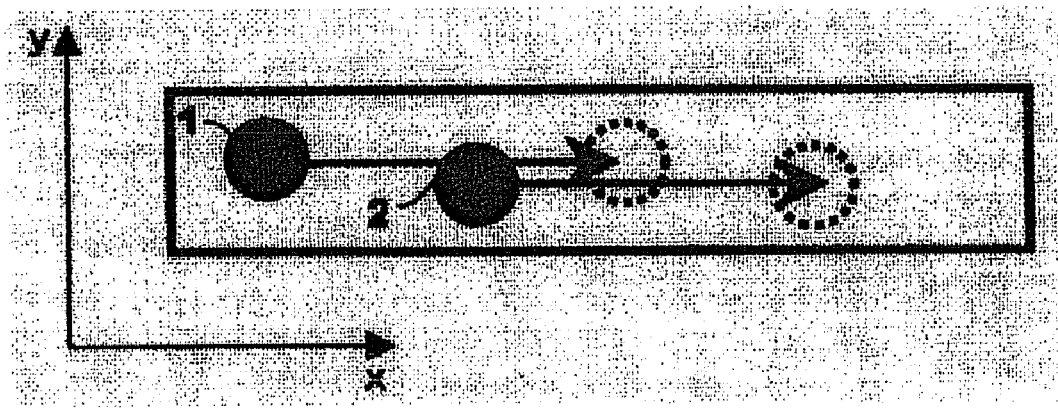
FIG. 4 is a typical view for explaining PIV processing.
Figure 5:
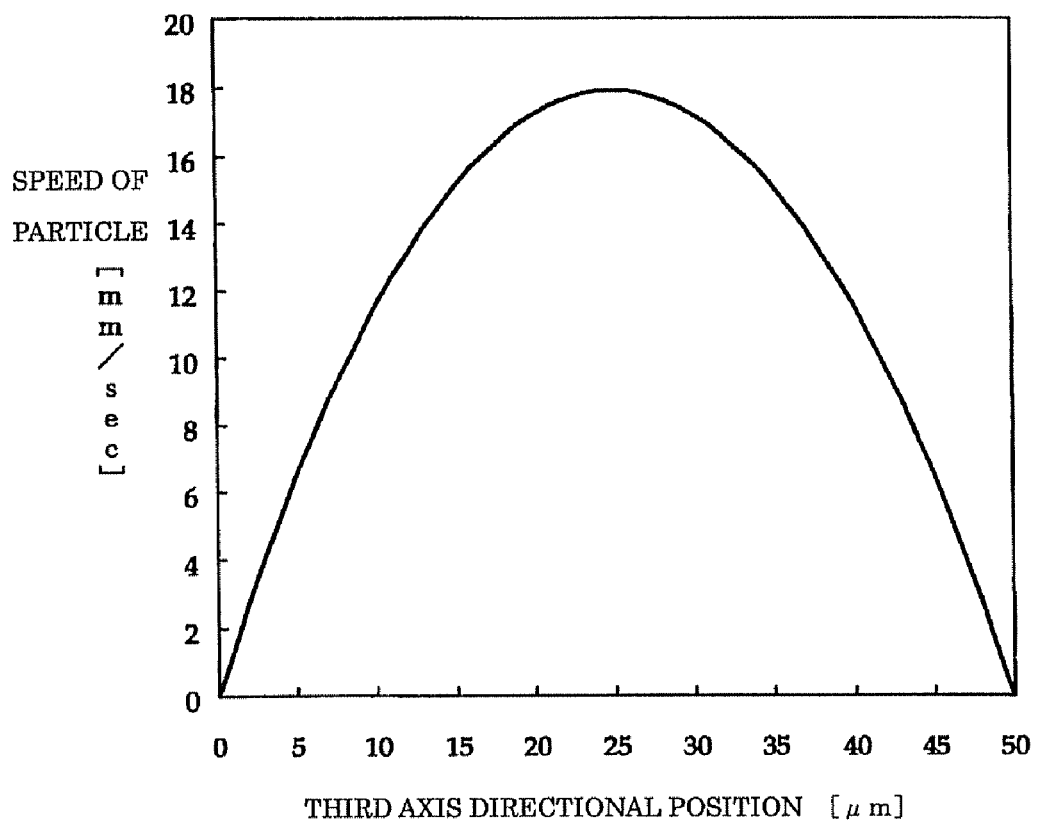
FIG. 5 is a view showing a relation between particle speed and a position in a third axial direction.
Figure 6:
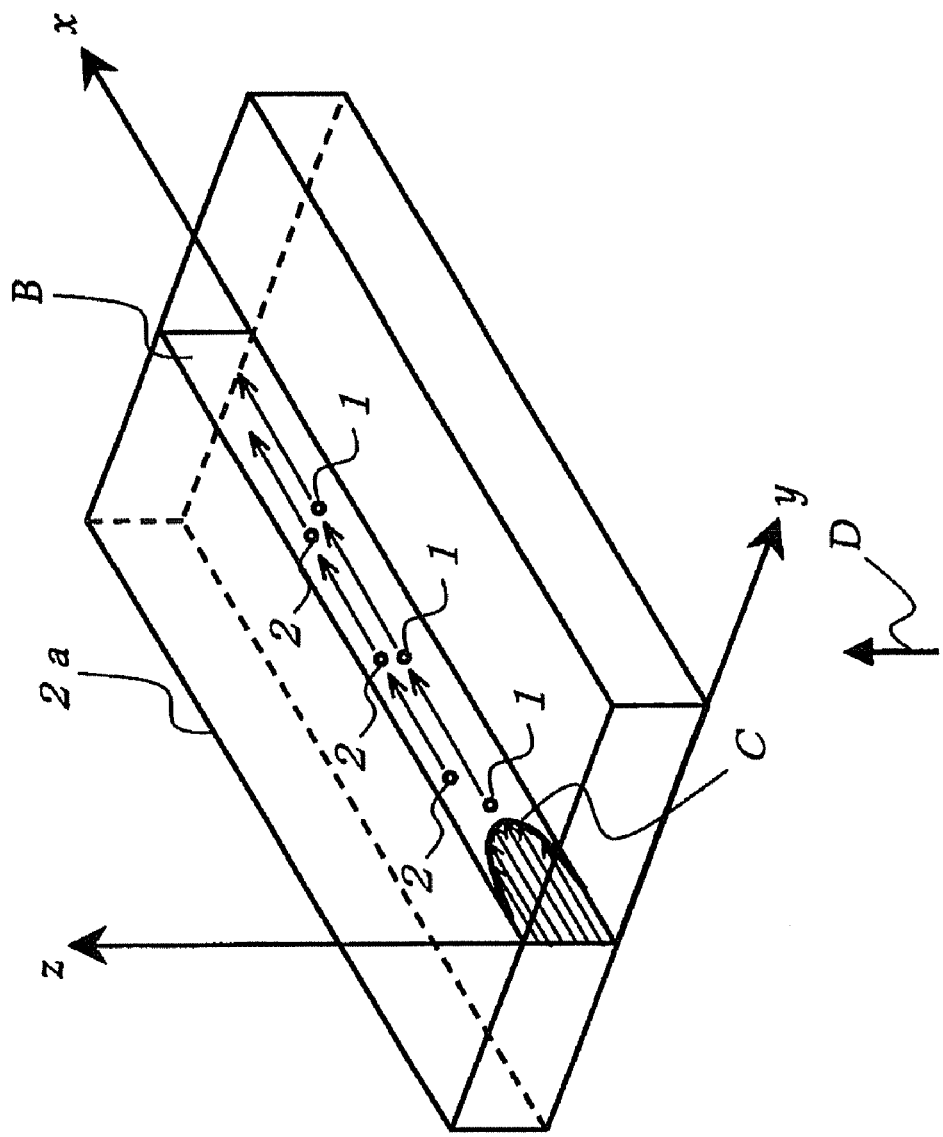
FIG. 6 is a typical view of flowing state of particles in a micro-channel.
Figure 10:
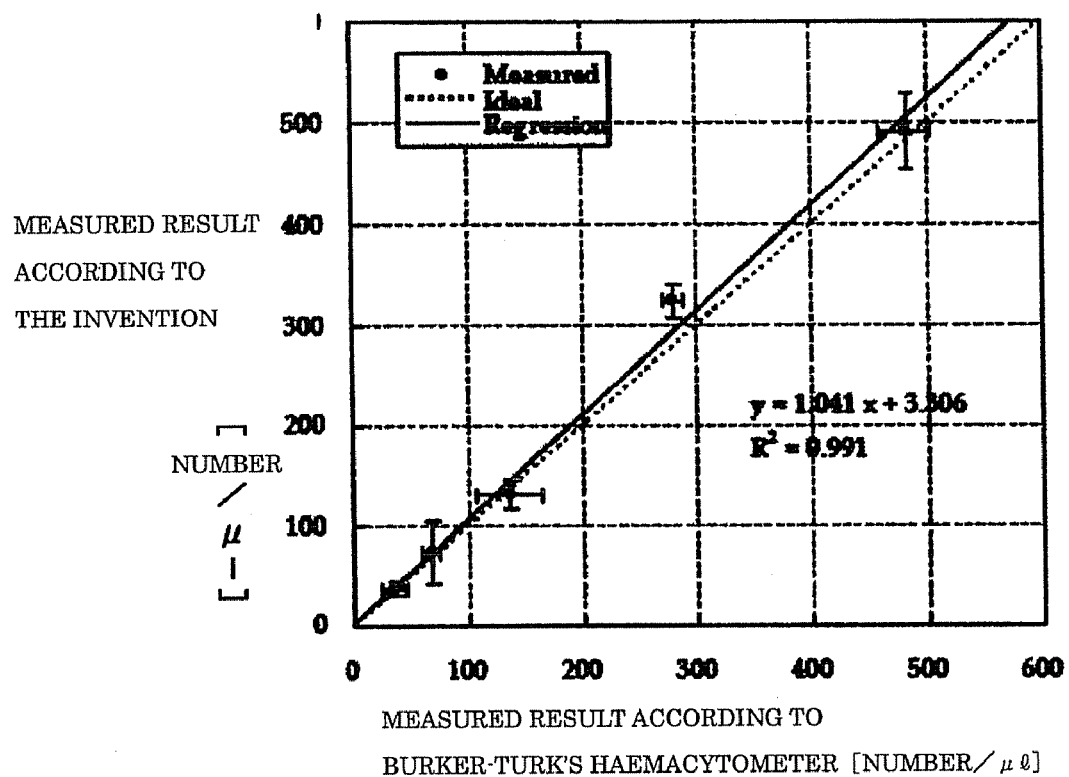
FIG. 10 is a view for comparing particle diameter measured through the device of the invention $d_y$, and particle diameter measured through Burker-Turk type of haemacytometer $d_x$ with each other.
Figure 11:
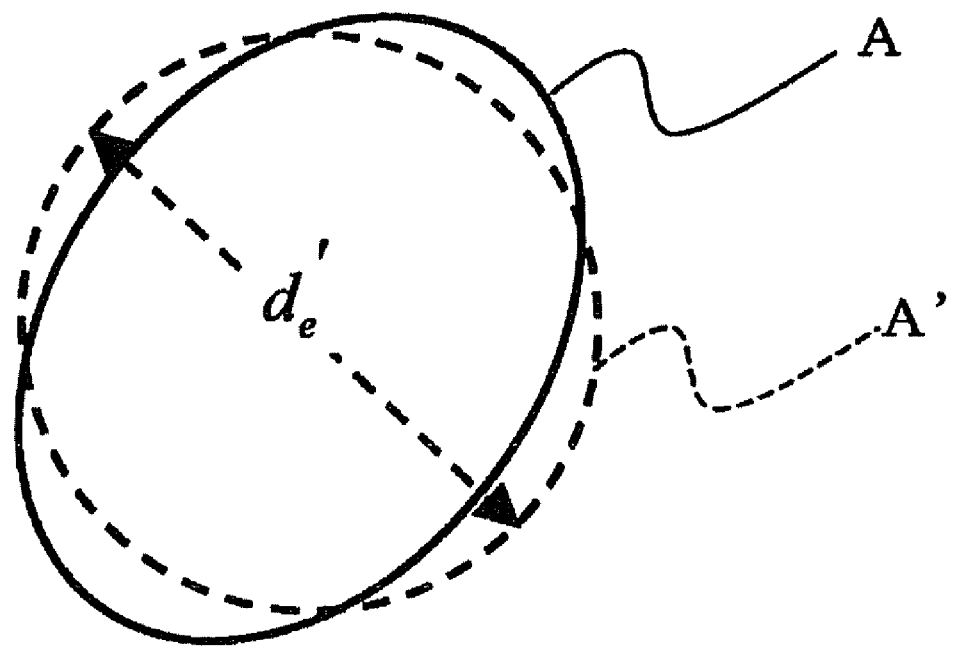
FIG. 11 is a typical view for explaining conditions for computing apparent particle diameter de'.
Figure 13:
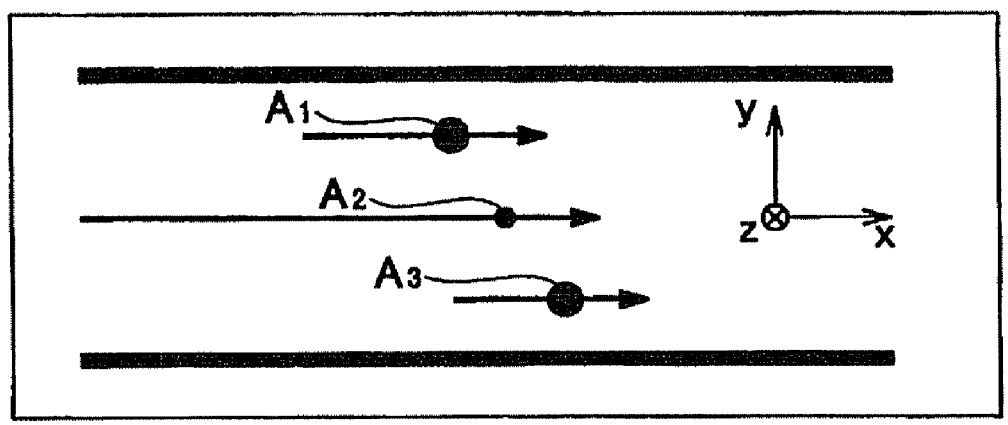
FIG. 13 is a typical view showing an image of three particles obtained by imaging means.
Figure 14:
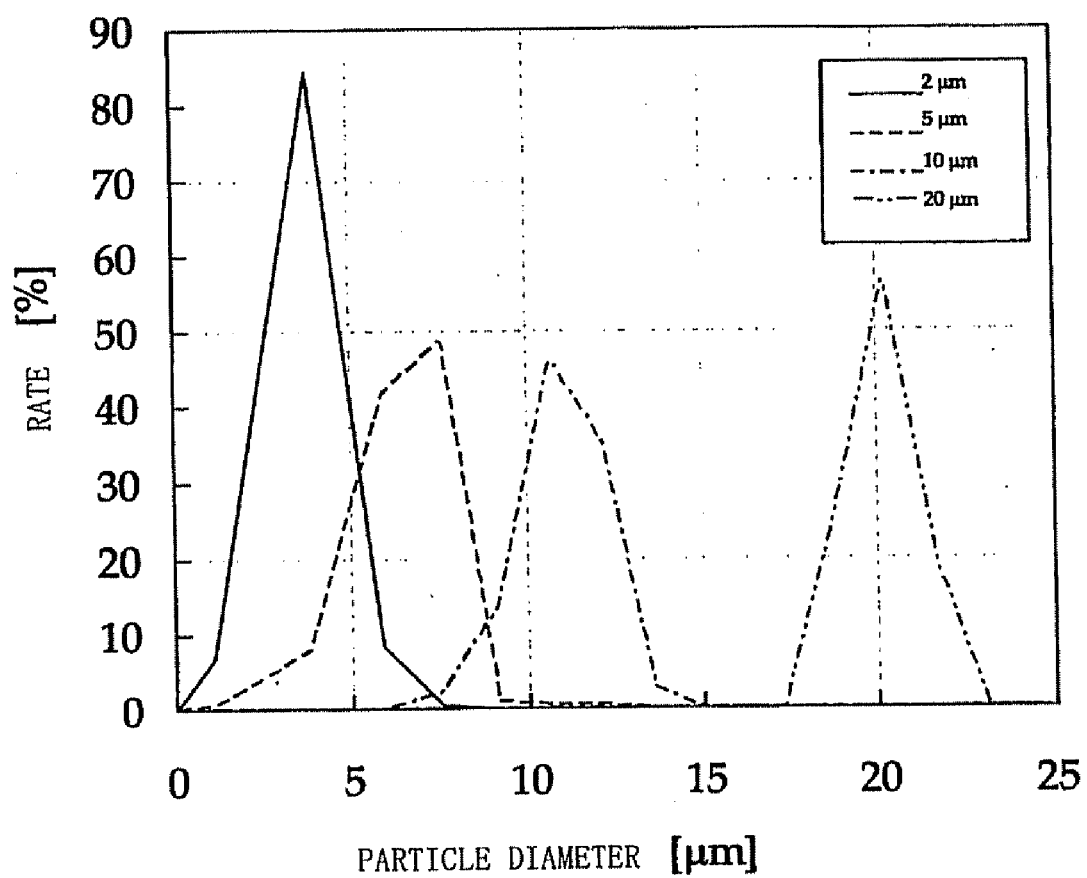
FIG. 14 is a view for explaining effects of the invention.

A best mode for carrying out the invention is now mentioned, referring to FIGS. 1 through 14. FIG. 1 is a block diagram showing an example of a structure of an important portion (data processor) of a particle measuring device according to the invention, FIG. 2 is a typical view showing the whole structure of the particle measuring device according to the invention, FIG. 3(a), (b) are views showing two stationary images (photographs) obtained by imaging means, FIG. 3(c) is a view (photograph) of a differential image between both stationary images and FIG. 4 is a typical view for explaining PIV processing. Besides, FIG. 5 is a view showing a relation between particle speed and a position in a third axial direction, FIG. 6 is a typical view of flowing state of particles in a micro-channel, FIG. 7 is a typical view showing such a state that a particle catches up to the particle and passes, FIG. 8 is a typical view showing flowing forms of particles, and FIG. 9 is a typical view showing another flowing forms of particles. FIG. 10 is a view for comparing particle diameter measured through the device of the invention $d_y$ and particle diameter measured through Burker-Turk type of haemacytometer $d_x$ with each other, FIG. 11 is a typical view for explaining conditions for computing apparent particle diameter $d_e'$. FIG. 12 is a typical view of flowing of particles seen from a second axial direction, FIG. 13 is a typical view showing an image of three particles obtained by imaging means, FIG. 14 is a view for explaining effects of the invention.

The particle measuring device according to the invention is one for measuring flowed particles based upon the image data, and concretely speaking, such device measures number of particles flowed in a predetermined time, particle speed and particle diameter.

It is necessary to correspond respective timing of obtaining measurement data, such as number, speed and diameter of particles, with each other in such a condition that many particles flow in succession. If respective timing are different in the three measurements, particle number of which is counted, particle speed of which is measured and particle diameter of which is measured are respectively different, so that it is meaningless to associate obtained measurement data with each other. Then, respective measurement values are associated with each other through associating means 73 mentioned hereinafter in the invention.

A concrete structure of such particle measuring device is now mentioned, referring to drawings.

The particle measuring device according to the invention is one denoted with a reference number 1 in FIG. 2, and has a micro chemical chip 2 with a micro-channel 2a. An upper stream side of the micro-channel 2a communicates with a container ("the sample container" in the specification) 3, and fluid mixing particles therein is entered in the sample container 3. On a lower stream side, flow measuring means 4 for measuring flow of fluid flowed down from the micro-channel 2a is located, and at a lower stream side of the flow measuring means 4, a micro pump 5 is located. By driving the micro pump 5, fluid mixing particles therein in the sample container 3 flows in the micro-channel 2a and the flow is measured by the flow measuring means 4. The device in the figure has the micro pump 5 at the lower stream side of the flow measuring means 4, but may be located at another place.

"Fluid" in the specification means "liquid", "gas", "two-phase fluid of liquid-gas", "two-phase fluid of liquid-solid", "two-phase fluid of gas-solid", or "multi-phase fluid of liquid-gas-solid". The invention can be used for measuring particle diameter of platelets in blood. Blood plasma, platelets, erythrocytes and leucocytes are included in blood. In this case, blood plasma corresponds to the liquid, the platelets correspond to the particles, erythrocytes correspond to the solid, and blood itself corresponds to multi-phase fluid of liquid-gas-solid.

The micro-channel 2a used in the invention has extremely small width and depth (for example, width is 200 μm and depth is 100 μm), which Reynolds number (for example, 0.35 to 1.4 or so) is much smaller than critical Reynolds number (about 2000). In such a micro-channel, fluid flows, forming laminar flow.

The flow measuring means 4 as shown in FIG. 2 is comprised of a container 40 for storing fluid flowed out of the micro-channel 2a, a weight measuring portion (electronic balance) 41 for measuring weight of fluid stored in the container 40, and a flow computing portion 42 for computing flow Q (flow at a unit of μl/s) based upon measured result by the electronic balance 41 (weight data of sample) and time data. The container 40 in FIG. 2 is a sealing container, and sample flows from the sample container 3 to the micro-channel 2a, and the container 40 by sucking air in the container through the pump 5. The flow measuring means having another structure may be used in the invention, and may be located at a position excluding on the lower stream side of the micro-channel 2a.

Besides, the particle measuring device 1 has imaging means 6 for imaging the micro-channel 2a from a direction (−z direction) almost orthogonal to a fluid flowing direction x in order to image particles flowed in the micro-channel 2a. Preferably, the imaging means 6 is comprised of a camera 60 for imaging moving images, a light source 61 for lighting the micro-channel 2a, and lens 62, 63. Well-known camera, such as a CCD camera, high speed CCD camera, an EMCCD camera, an IICCD camera and a CMOS camera, may be used as the camera 60. Besides, well-known light source, such as a halogen lamp, a xenon lamp, a white LED, may be used as the light source 61. Image data GD imaged by the imaging means 6 is transmitted to a data processor (personal computer) 7, and the processor computes particle diameter and the like. The obtained image may be sent through US B2.0 interface or a video capture board.

In the specification, "first axial direction" is fluid flowing direction (particles are mixed in fluid) (see reference mark x), and "third axial direction" is the direction almost orthogonal to the first axial direction x and the direction where the imaging means 6 images the micro-channel 2a (see reference mark z), and "second axial direction" is the direction almost orthogonal to the first and third axial directions (see reference mark y) for easy understanding.

As exemplarily shown in FIG. 1, the data processor 7 has (1) particle speed measuring means 70 for measuring speed u of particle flowed based on the image data GD imaged by the imaging means 6,
(2) particle number counting means 71 for counting number n of particles flowed in a predetermined time based on the image data GD imaged by the imaging means 6,
(3) particle size measuring means 72 for measuring diameter dp3 of particle flowed based upon the image data GD imaged by imaging means 6, and
(4) data associating means 73 for controlling by associating measurement values u, n, dp3 measured by the respective measuring means 70, 71, 72 with time based upon time data at a time when the respective measuring means 70, 71, 72 measure. These means 70, 71, 72 and 73 are now mentioned in detail.

(1) Particle Speed Measuring Means 70

Fluid flows in the micro-channel 2a, forming flow layers, as mentioned above, each particle flows, keeping a distance between the particle and a wall face of the micro-channel 2a constant, that is, without keeping close to or away from the wall face, and the speed of each particle seldom changes. Therefore, the particle speed measuring means 70 may be comprised of
a movement distance computing portion 701 for computing a movement distance of each particle by image processing of two or more stationary images imaged by the imaging means 6, and
a particle speed computing portion 702 for computing the speed by dividing the computed movement distance by imaging interval Δt.
Preferably, the movement distance computing portion 701 forms an differential image similar to a differential image forming portion 711 mentioned hereinafter, and computes the movement distance by executing a well-known image processing.

(2) Particle Number Counting Means 71

The particle number counting means 71 may be comprised of the differential image forming portion 711 for forming a differential image from two sheets of stationary images (image data) imaged by the imaging means 6, a relating portion 712 for relating a particle to a position to which the particle moves, and a particle number counting portion 713 for counting number of the particles based upon data from the relating portion 712. FIG. 3(a), (b) are two sheets of stationary images imaged by the imaging means 6, for example. Four particles shown in FIG. 3(a) are moved to positions shown in FIG. 3(b) after a predetermined time. Besides, FIG. 3(c) is a differential image of the two sheets of stationary images, and proper offset is added thereto. White points shown in the differential image are particles imaged in a later image and black points are particles imaged in a former image. Image processing is executed with two threshold values, a black color rather than gray color of a background and a white color rather than gray color, and black points and white points are extracted. After extracting the particles, a PIV processing (Particle Image Velocimetry) is executed by the relating portion 712 so as to relate the particles, and thereafter, the particle number counting portion 713 counts number of the particles.

The PIV processing through the relating portion 712 is now mentioned.

In a general PIV processing wherein to which direction a particle moves is unclear, an image is divided into several areas, and a portion having the highest correlation with the area is found, and amount of movement is obtained. But, its computing is voluminous in such a method. In case of the device according to the invention, fluid flows in x direction, forming laminar flow, and particles only move in x direction and almost never move in another directions, such as y direction and z direction. In other words, particles denoted with numerals 1, 2 only move in x direction as they are (see dotted line). The processing through the relating portion 712 is executed on the assumption of the above-mentioned, and a coordinate of center of gravity of each particle is computed with a known image processing wherein respective coordinates of pixels of respective objects are added together, and the added is divided by area), and the particle which y coordinate is the same and x coordinate increases is searched from a second image. According to this method, the computing volume can be widely reduced.

In FIG. 4, the particles 1, 2 are visible in the first stationary image, and two particles shown with a dotted line are visible in the second stationary image. In an actual image, such a pattern is not limiting. For example, the particle 1 passes the particle 2 as shown in FIG. 7, or the particles move as shown in FIG. 8 or FIG. 9. Such movements are now mentioned.

<Passing of Particle (Overlapping)>

As mentioned above, fluid flows, forming laminar flow and the speed of the individual particle almost never changes. But, the speed of the fluid itself flowing forming laminar flow is different, depending on a distance from a wall face of channel, and the speed of the particle is different according to the distance from the wall face of the channel. FIG. 5 is a view showing an example of a relation between the speed of the particle and the third axis directional position, and the third axis directional position, zero (0) and 50 μm show the wall face of the channel, and the third axis directional position 25 μm shows a center of the channel. That is, the speed of the particle become higher as the particle departs from the wall face, and a curved line, such as a parabola in the shape of a convex, is drawn in an upper direction. In consideration of a virtual face B in the micro-channel 2a as shown in FIG. 6, the relation as shown in FIG. 5 is formed in connection with the particles flowed along the virtual face B (Of course, the relation as shown in FIG. 5 is also formed in connection with a x-y face orthogonal to the virtual face B), and a speed distribution curve becomes one denoted a mark C. And, the particle speed becomes low as the particle is close to the wall face, and the particle speed becomes high as the particle departs from the wall face. In the following descriptions, the particle 2 flowing at the position close to the wall face of the channel and the particle 1 flowing at a position departing from the wall face are considered. In such a case, it is found that the speed of the particle 2 on the upper side is lower than one of the particle 1 on the lower side.

FIG. 7 (*a*) to (*c*) are typical views showing images obtained by imaging the above-mentioned two particles. Its imaging direction is a direction as shown with an arrow D in FIG. 6. The particle 1 as shown in FIG. 7(*a*) is faster than the particle 2, and catches up to the particle 2 in the next obtained image (see FIG. 7 (*b*)), and furthermore passes the particle 2 in further next image (see FIG. 7 (*c*)).

According to a timing of imaging or the speed of the particles, the particle 1 may not be found in the obtained image as shown in FIG. 8(*a*), and may appear at a position passing the particle 2 in the next obtained image (Frame-in).

Although the two particles appear in the obtained image as shown in FIG. 9(*a*), one of two may disappear in the next image as shown in FIG. 9(*b*) (Frame-out).

For correct association through the relating portion 712, it is necessary to understand various kinds of movements of the particles and to compensate based upon such movements. Then, preferably, the particle number counting means 71 has a particle position predicting portion 714, for predicting the position of the particle in the next stationary image from speed u of each particle obtained through the particle speed measuring means 70, and a particle movement predicting portion 715, for predicting movements of the particles based on data of the particle position predicting portion 714, such as overlapping of the particles, superimposing, frame-in and frame-out, and a particle number compensating portion 716, for compensating measurement data of the particle number counting portion 713 based upon data of the particle movement predicting portion 715.

The inventors have measured number of the particles of five kinds of samples with the above-mentioned particle number counting means 71 and a Burker-Turk's haemacytometer, and compared both with each other. FIG. 10 is a view for comparing a particle diameter $d_y$ measured by the device of the invention and particle diameter $d_x$ measured by the Burker-Turk's haemacytometer with each other. Needless to say, an ideal is that the relation between $d_y$ and $d_x$ is equal to the relation $d_y = d_x$ (a straight line passing through an origin and the straight line rising in a right direction, having an inclination 45 degree. When plotting measurement result by the device of the invention, $d_y = 1.041 d_x + 3.306$, and it was found that the relation is close to $d_y = d_x$. Therefore, it was found that the measurement result by the particle number counting means 71 was accurate.

(3) Particle Size Measuring Means 72

The particle size measuring means 72 has a first particle size computing means 72A, for computing an apparent particle diameter de' on the image based upon image data GD obtained by the imaging means 6, and such apparent particle diameter de' is computed by the computing means 72A. Preferably, the first particle size computing means 72A has an area computing portion 721, for computing an area S of the particle based upon the image data GD, and a particle size computing portion 722, for computing the apparent particle diameter de' based upon the area S computed by the area computing portion 721 and the following expression. That is, the first particle size computing means 72A computes the particle diameter de', assuming that the particle is a sphere (a circle on the image) as shown with a broken line A' although the particle is actually an oblate as shown with a full line A in FIG. 11. The diameter de' is computed by the first particle size computing means 72A, but another structure for computing a radius is not excluded from the scope of the invention. Such an area S may be computed with the above-mentioned differential image.

$$d'_e = 2\sqrt{\frac{S}{\pi}} \qquad \text{[Expression 4]}$$

An error due to the position of the particle in the third axial direction may be included in the result computed with the above-mentioned expression. Such a point is now mentioned, referring to FIG. 12 and FIG. 13.

In FIG. 12, the camera is denoted with a reference number 60, and a focal face of the camera is denoted with a reference numeral 60a. In the case of FIG. 12, a middle particle A2 flows on the focal face 60a, an upper particle A1 in the figure flows on a side far from the camera 60 with respect to the focal face 60a, and an lower particle A3 in the figure flows on a side close to the camera 60 with respect to the focal face 60a. FIG. 13 is a typical view of an image of these three particles. FIG. 12 and FIG. 13 are similar views, but are different in their view directions. FIG. 12 is a view seen from the second axis directional side (+side of y axis), and FIG. 13 is a view seen from one side of the third axis (z axis) (view of the image obtained by imaging means). Although the particle A2 flowing on the focal face 60a is imaged as a smallest one (see FIG. 13), the other two particles (the particle A1 flowing on the side far from the focal face 60a and the particle A3 flowing on the side close to the focal face 60a) are imaged as blurred big ones in comparison with the middle particle A2 (see FIG. 13). For this reason, the apparent diameters de' of both particles A1, A3 are computed as ones bigger than the actual ones. In order to delete such errors, it is necessary to compensate the particle diameter de' according to amount of deviation (see reference marks Δz1 and Δz3 of FIG. 12) from the focal face 60a. Preferably, the particle size measuring means 72 has a particle size compensating portion 72B, for compensating a computed result de' of the first particle size computing means 72A based upon amount of deviation Δz of the particle in the third axial direction with respect to the focal face 60a of the imaging means 6. Such particle size compensating portion 72B is now mentioned.

As shown in FIG. 1, the particle size compensating portion 72B has a second axis directional position measuring portion 723, for measuring a position y of the particle in the second axial direction from the image data GD, a third axis directional position computing portion 724, for computing a position of the particle in the third axial direction z from measured result Q of the flow measuring portion 4, computed result u of the particle speed measuring means 70, measured result y through the second axis directional position measuring portion 723 and the Navier-Stokes equation regarding the fluid flowing in the micro-channel 2a, a deviation computing portion 725 for computing amount of deviation Δz of the particle in the third axial direction with respect to the focal face 60a of the imaging means 6 based upon the computed result z of the third axial directional position computing portion 724, and a second particle size computing portion 726, for computing the second particle diameter dpi after compensating the amount of deviation Δz from the computed result Δz of the deviation computing portion 725 and the computed result de' of the first particle size computing means 72A.

The particle size measuring means 72 may have a blur predicting means 72c, for predicting a degree of blur of the image of the particle (relative rate between the apparent particle diameter de' and the actual particle diameter) based upon the computed result Δz of the deviation computing portion 725, and the particle diameter is compensated according to the degree of blur thereby.

The above-mentioned third axis directional position computing portion 724 and the Navier-Stokes equation are now mentioned.

An analytical solution of flowing speed of the Navier-Stokes equation in a case where the micro-channel 2a has a rectangle section is as follows.

$$u = \frac{Q}{\frac{2D^3W}{3} + \frac{256D^4}{\pi^5}\sum_{n=1,3,5,\ldots}^{m}\left\{\frac{\frac{1}{n^5}\cos(n\pi)}{\tanh\left(\frac{n\pi W}{4D}\right)}\right\}} \times$$ [Expression 5]

$$\left\{\frac{z}{2}(2D-z) - \frac{16D^2}{\pi^3}\sum_{n=1,3,5,\ldots}^{m}\frac{1}{n^3}\sin\left(\frac{n\pi}{2D}z\right)\frac{\cosh\left(\frac{n\pi}{2D}y\right)}{\cosh\left(\frac{n\pi W}{4D}\right)}\right\}$$

where
D=half of width of micro-channel in the third axial direction (see FIG. 3)
W=width of micro-channel in the second axial direction (see FIG. 3)
u=flow speed of particulate
Q=flow
y=second axis directional position of the particulate
z=third axis directional position of the particulate.

In this case, values of D and W are known values, a value of half of a height of the channel and a width of the channel, and the flowing speed (the speed of the particle) u is computed by the particle speed measuring means 70, the flow Q is computed by the flow measuring means 4, and the position of the particle in the second axial direction is measured by the second axis directional position measuring portion 723. Then, any values are known values. Therefore, the position of the particle in the third axial direction z is obtained with the above-mentioned equation.

By doing so, a relation between the particle speed u and the third axis directional position z is obtained.

$Q=0.028$ [μl/s]

$D={}^{50}\!/_2=25$ [μm]

$W=200$ [μm] [Expression 6]

In a case of the above-mentioned expression, the relation between the particle speed u and the third axis directional position z ($0\leq z\leq 25$) becomes one shown in FIG. 5, and the third axis directional position z is computed based upon the computed result u of the particle speed measuring means 70.

The apparent particle diameter de' computed by the first particle size computing means 72A may be bigger one than the actual one due to a phenomenon of diffraction of light. In a case where the particle diameter on the image is de, the actual particle diameter is dp, an airy disk diameter due to diffraction is ds, a magnification of an imaging optical system is M, wavelength of light is λ, and number of openings is NA, the following expression is formed. For example, the apparent particle diameter de may be ≈19 through 30 μm in a case where M=5, λ=visible light (400 through 700 nm), and NA=0.18 although the actual particle diameter dp is 2 μm. In other words, the apparent particle diameter is a convolution of the actual particle diameter and PSF, and the particle diameter computed by the first particle size computing means 72A from the image data GD becomes a very big value than the actual particle diameter dp.

$$d_e = \sqrt{M^2 d_p^2 + d_s^2}$$ [Expression 7]

$$d_s = \frac{1.22(1+M)\lambda}{NA}$$

Preferably, the third particle size computing means (see reference number 72D of FIG. 1) is provided with the data processor 7, and a deconvolution procedure is executed in order to compensate the error due to a phenomenon of diffraction of light.

The inventors prepared four kinds of samples,
pure water including polystyrene particles each diameter of which is 2 μm therein
pure water including polystyrene particles each diameter of which is 5 μm therein
pure water including polystyrene particles each diameter of which is 10 μm therein
pure water including polystyrene particles each diameter of which is 20 μm therein.

Then, the particle diameter of each sample has been measured. The result is shown in FIG. 14, and it was found a measurement accuracy of the device is high.

If the particle diameter changes together with time, the particle diameter may be momently computed, or an average particle diameter within a predetermined time may be obtained. In the former case, time data may obtained by the data associating means 73, and the time data may be associated with the measured result of the particle diameter.

Second Embodiment

Figure 15:
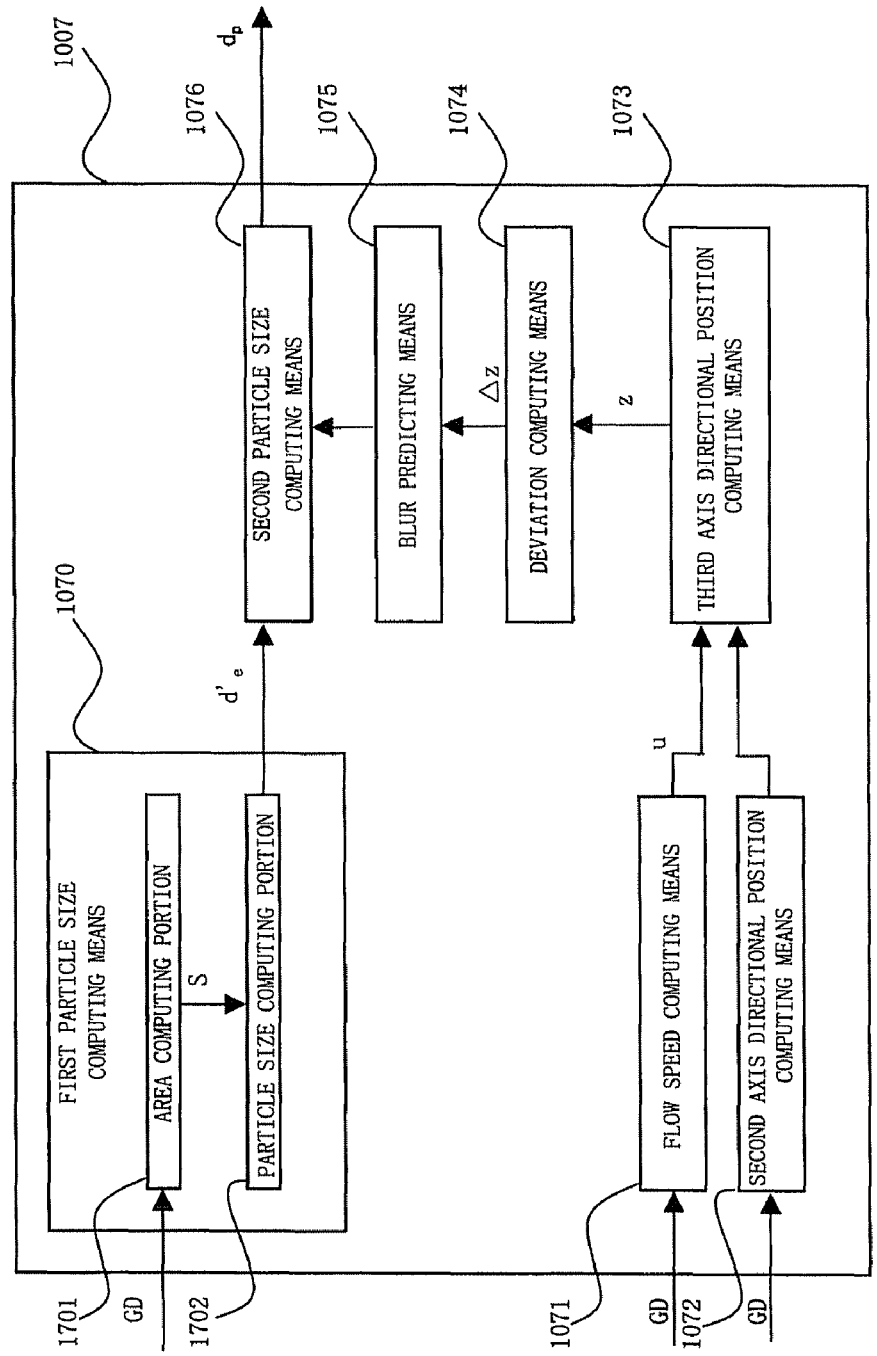
FIG. 15 is a block diagram showing an example of a structure of a important portion (data processor) of a particle size measuring device according to the invention.
Figure 16:
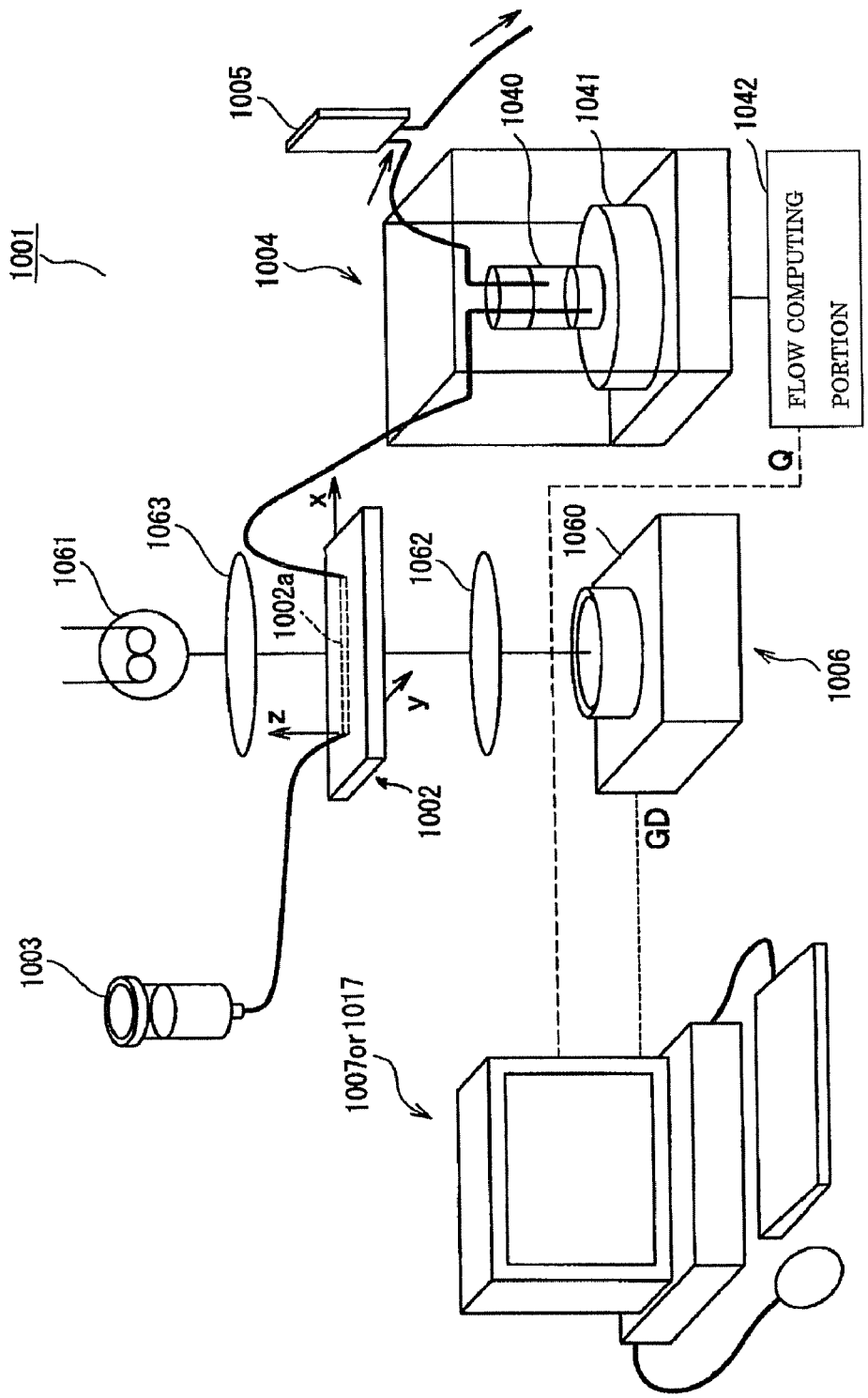
FIG. 16 is a typical view showing an example of the whole structure of the particle size measuring device according to the invention.
Figure 17:
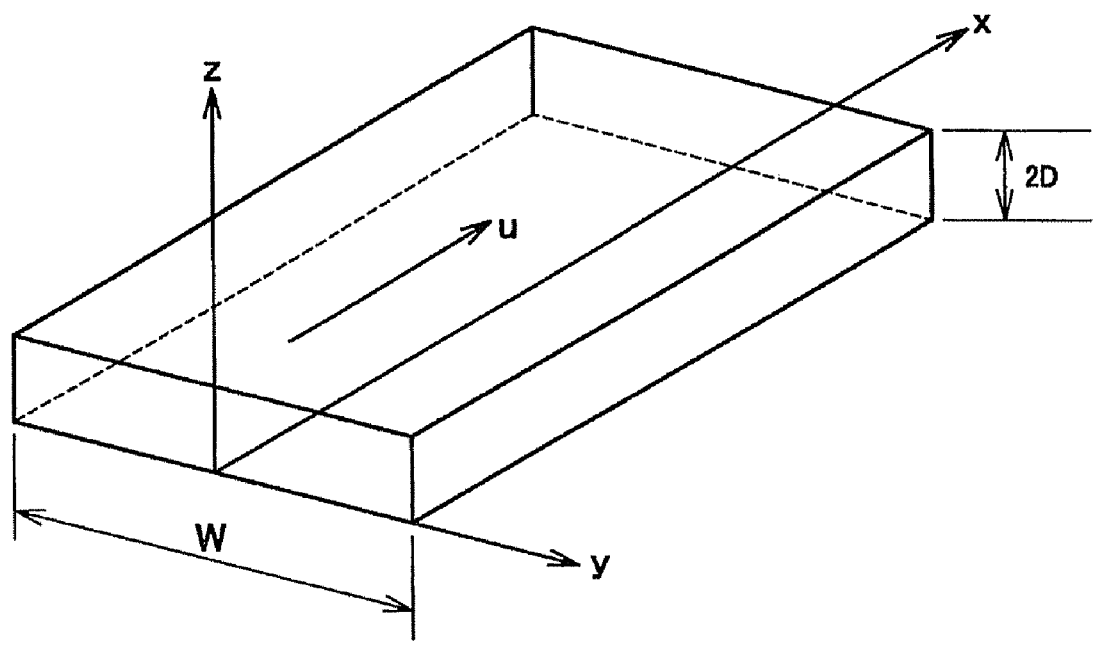
FIG. 17 is a typical view for explaining a form of the micro-channel.
Figure 18:
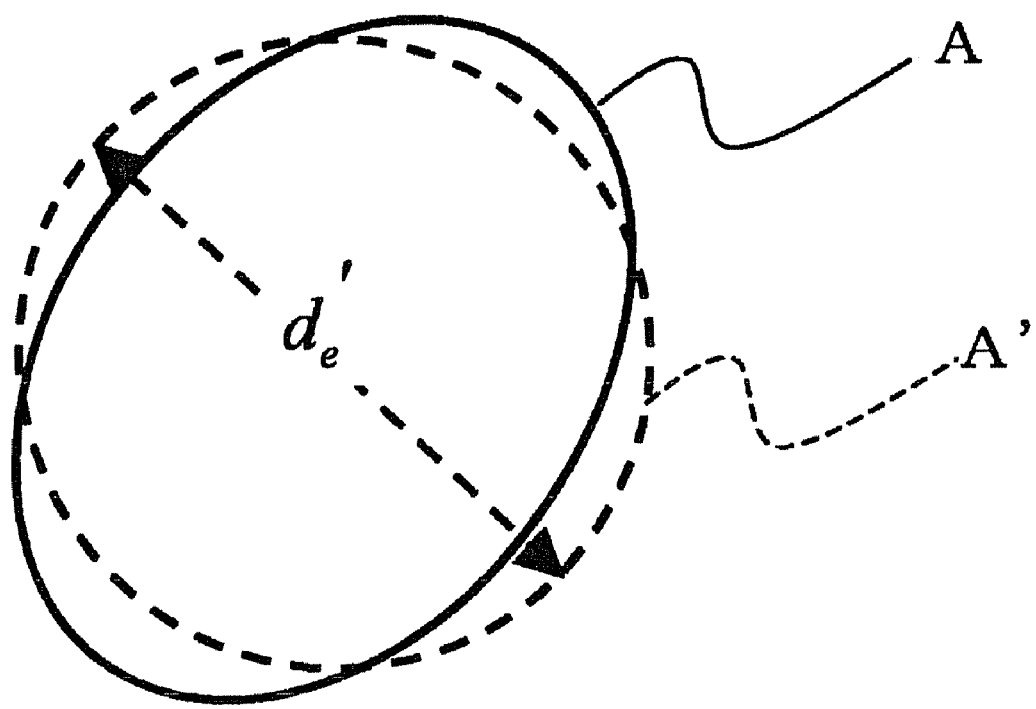
FIG. 18, is a typical view for explaining conditions for computing apparent particle diameter de'.
Figure 20:
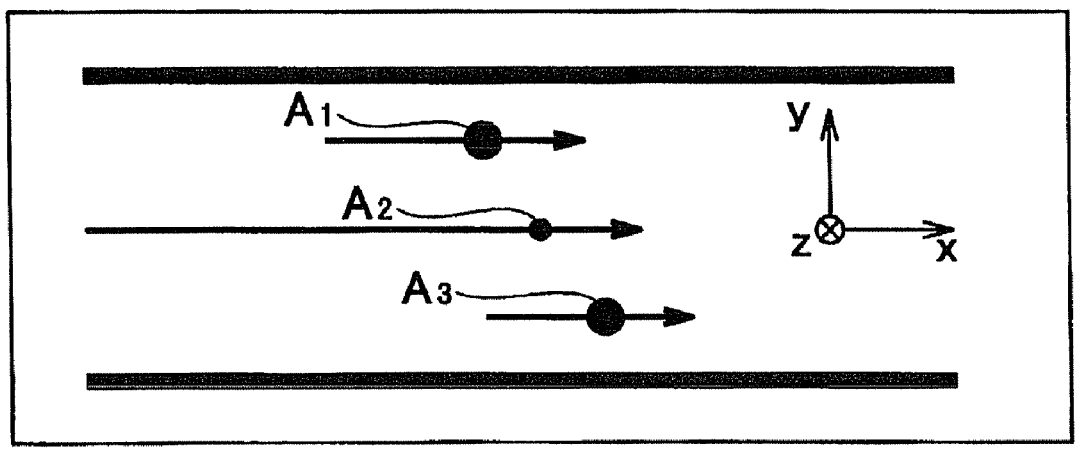
FIG. 20 is a typical view showing an image of three particles obtained by the imaging means.
Figure 21:
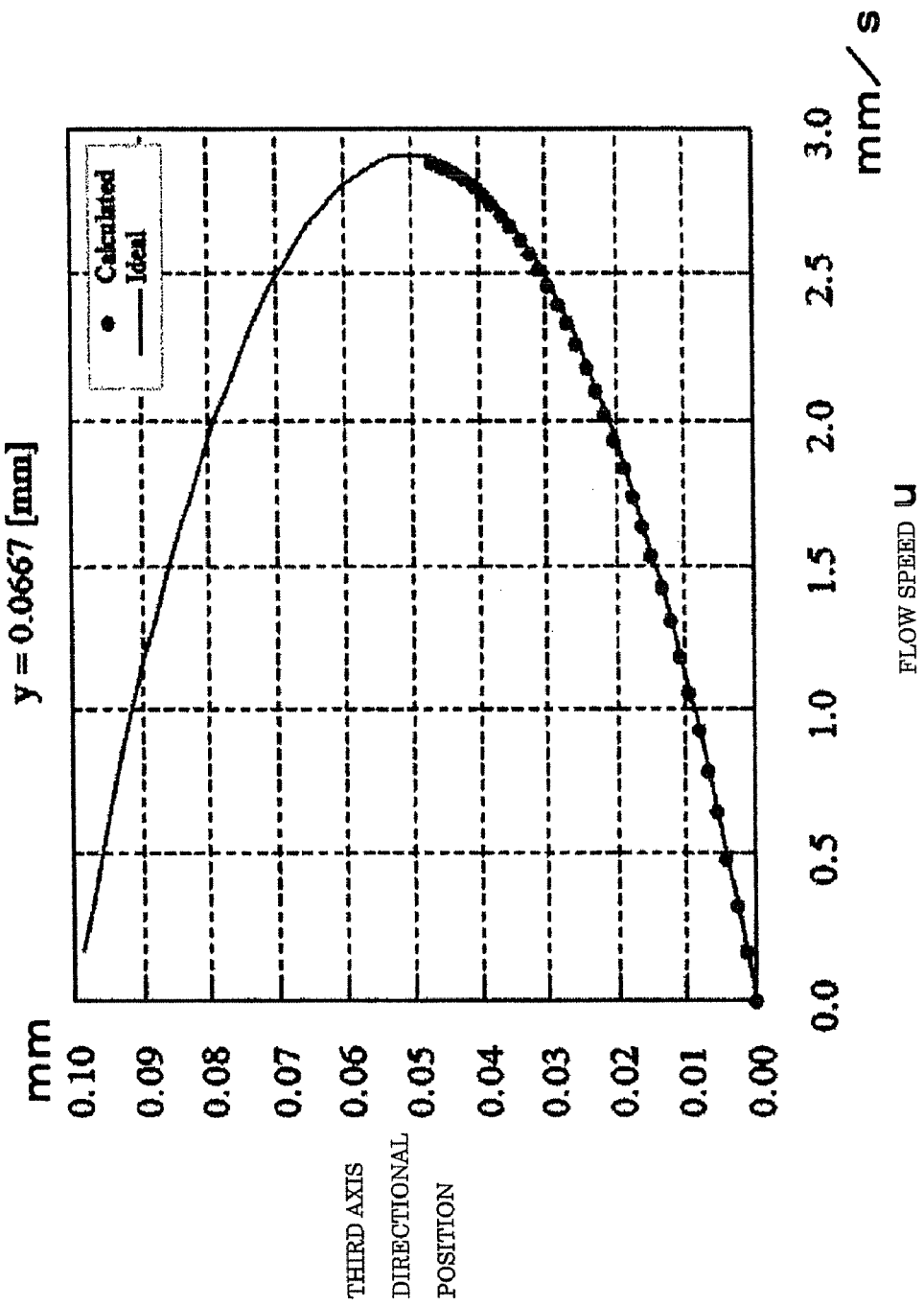
FIG. 21 is a view showing a relation between flow speed and the third axial directional position.
Figure 23:
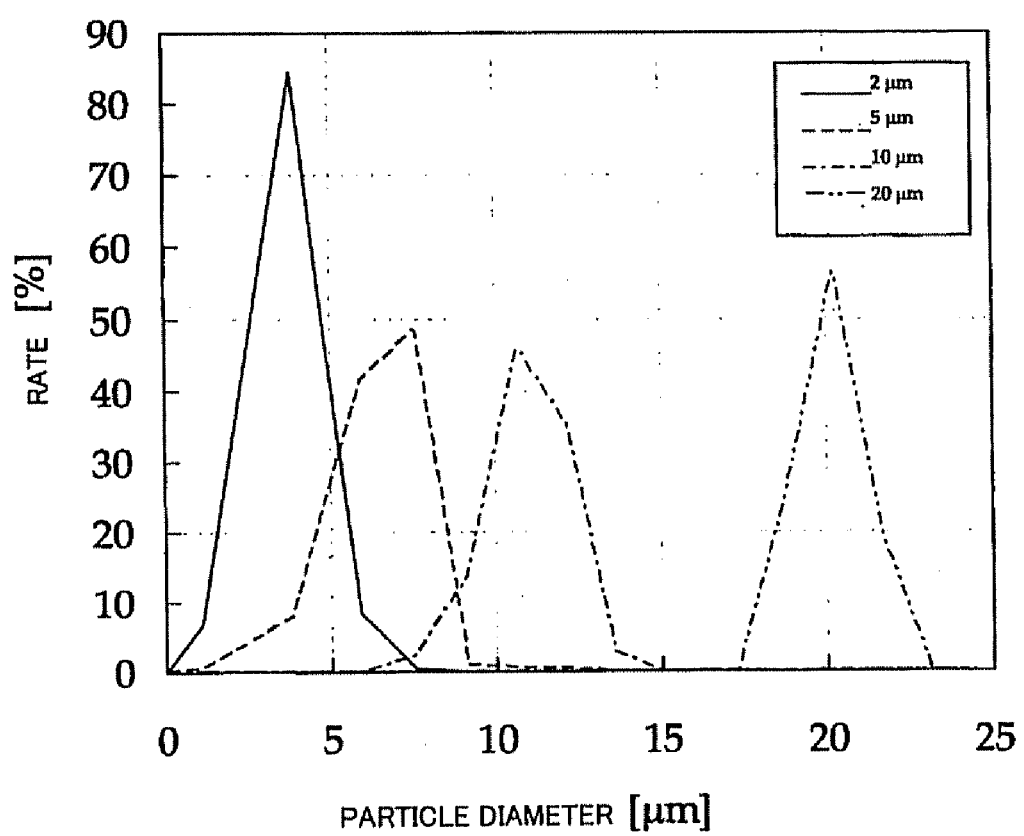
FIG. 23 is a view for explaining effects of the invention.
Figure 24:
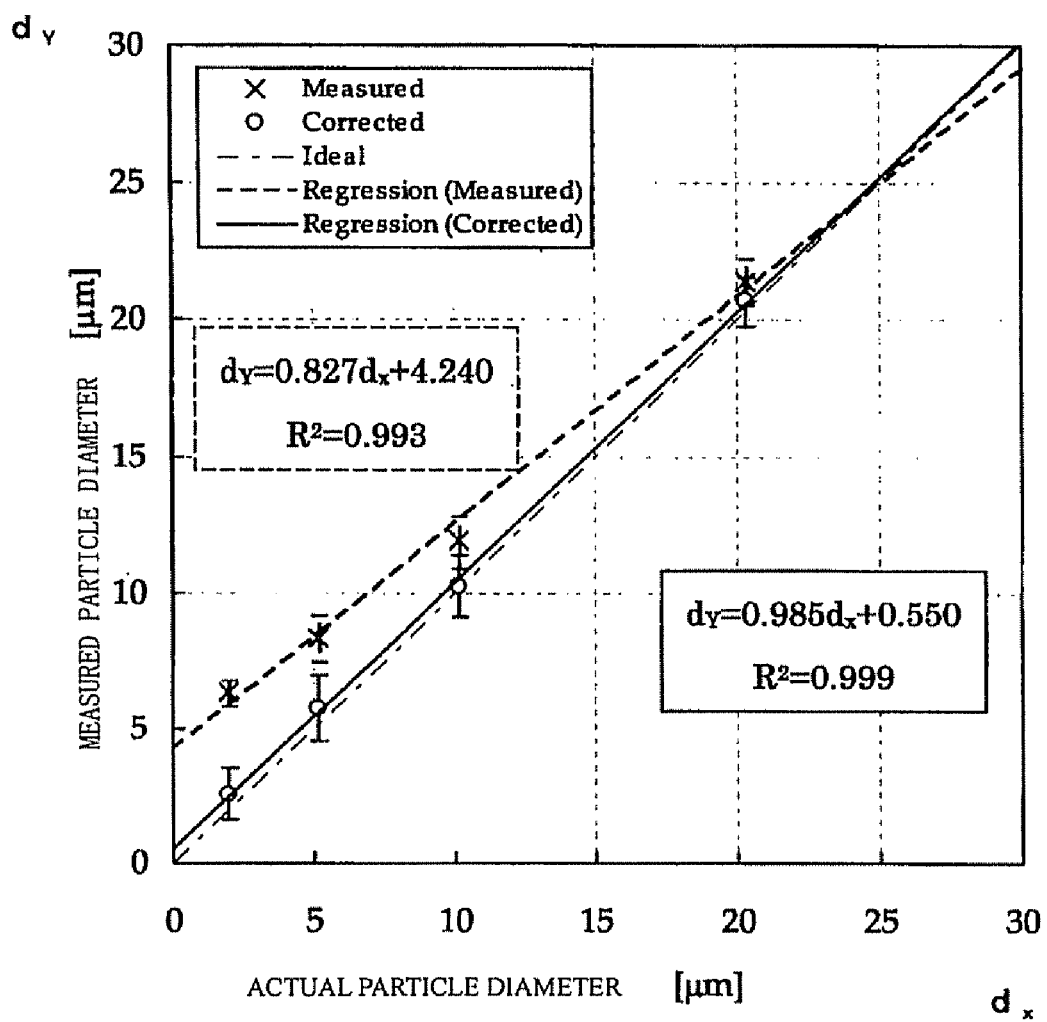
FIG. 24 is a view showing a relation between measured value of particle diameter $d_y$ and actual particle diameter $d_x$.

A best mode for carrying out the invention is now mentioned, referring to FIGS. 15 through 24. FIG. 15 is a block diagram showing an example of a structure of an important portion (data processor) of the particle size measuring device according to the invention, FIG. 16 is a typical view showing an example of the whole structure of the particle size measuring device according to the invention, FIG. 17 is a typical view for explaining a form of a micro-channel, and FIG. 18 is a typical view for explaining conditions for computing apparent particle diameter de'. And, FIG. 19 is a typical view showing flowing of particles which is seen from the second axial direction, FIG. 20 is a typical view showing an image of three particles obtained by imaging means, and FIG. 21 is a view showing a relation between flow speed and the third axis directional position. Besides, FIG. 22(a) is a view showing analysis result with no compensation through second particle size computing means, and FIG. 22(b) is a view showing analysis result with compensation through second particle size computing means. Furthermore, FIG. 23 is a view for explaining effects of the invention, and FIG. 24 is a view showing a relation between measured value of particle diameter $d_y$ and actual particle diameter $d_x$.

The particle size measuring device according to the invention is a device for measuring diameter of particles mixed in fluid, and proper embodiments are shown in FIGS. 15 and 16.

A reference number 1002 in FIG. 16 denotes a micro chemical chip having a micro-channel 1002a. An upper stream side of the micro-channel 1002a is communicated with a container 1003 ("sample container" in the specification), and fluid including particles therein is entered in the sample container 1003. On a lower stream side of the micro-channel 1002a, a flow measuring means 1004 for measuring flow of fluid flowed out of the micro-channel 1002a is located. And, a micro pump 1005 is located at the lower stream side of the flow measuring means 1004. The fluid in the sample container 1003 flows in the micro-channel 1002a by driving the micro pump 1005, and its flow is measured by the flow measuring means 1004. In this device, the micro pump 1005 is located at the lower stream side of the flow measuring means 1004, but this location is not limiting and the micro pump may be located at a another place.

"Fluid" in the specification means "liquid", "gas", "two-phase fluid of liquid-gas", "two-phase fluid of liquid-solid", "two-phase fluid of gas-solid", "multi-phase fluid of liquid-gas-solid". The invention can be used for measuring particle size of platelets in blood. Blood plasma, platelets, erythrocytes and leucocytes are included in blood. In this case, blood plasma corresponds to the liquid, the platelets correspond to the particles, erythrocytes correspond to the solid, and blood itself corresponds to multi-phase fluid of liquid-gas-solid.

The flow measuring means 1004 as shown in FIG. 16 is comprised of a container 1040 for storing fluid flowed out of the micro-channel 1002a, a weight measuring portion (electronic balance) 1041 for measuring weight of fluid stored in the container 1040, and a flow computing portion 1042 for computing flow (flow at a unit of μl/s) based upon measured result by the electronic balance 1041 and time data. The container 1040 in FIG. 16 is a sealing container, and sample flows from the sample container 1003 to the micro-channel 1002a, and the container 1040 by sucking air in the container through the pump 1005. The flow measuring means having another structure may be used in the invention, and the following measuring means may be located at a position excluding on the lower stream side of the micro-channel 1002a. Besides, the flow computing portion 1042 may be built in data processors 1007, 1017 mentioned hereinafter.

FIG. 17 is a perspective view typically showing the micro-channel (the perspective view of the micro-channel 1002a seen from an oblique upper side in FIG. 16). In the specification, "first axial direction" is fluid flowing direction (particles are mixed in fluid) (see reference mark x), and "second axial direction" is the direction almost orthogonal to the first axial direction (see reference mark y) and "third axial direction" is a direction almost orthogonal to the first axial direction and the second axial direction (see reference mark z) for easy understanding. Any form of the micro-channel 1002a is available as long as fluid flows therein, forming laminar flow. For example, width W in the second axial direction is 200 μm, depth (2D) in the third axial direction is 50 μM, and length in the first axial direction is 30 mm.

Besides, a particle size measuring device 1001 has imaging means 1006 for imaging the third axial direction z in order to image particles flowed in the micro-channel 1002a. Preferably, the imaging means 1006 is comprised of a camera 1060 for imaging moving images, a light source 1061 for lighting the micro-channel 1002a, and lens 1062, 1063. Well-known camera, such as a CCD camera, high speed CCD camera, an EMCCD camera, an IICCD camera and a CMOS camera, may be used as the camera 1060. Besides, well-known light source, such as a halogen lamp, a xenon lamp, a white LED, may be used as the light source 1061.

Image data imaged by the imaging means 1006 is transmitted to a data processor (personal computer) 1007, and the processor computes particle diameter and the like. The obtained image may be sent through US B2.0 interface or a video capture board.

As exemplarily shown in FIG. 15, the data processor 1007 may have
first particle size computing means 1070 for computing apparent particle diameter de' on an image based upon image data GD imaged by the imaging means 1006,
particle speed computing means 1071 for computing flow speed u of particle based on the image data GD,
second axis directional position measuring means 1072 for measuring a position of the particle in the second axial direction y from the image data GD.

The first particle size computing means 1070 may be comprised of an area computing portion 1701, for computing area S of the particle based upon the image data GD, and a particle size computing portion 1702, for computing the apparent particle diameter de' based upon the area S computed by the area computing portion 1701 and the following expression. That is, the first particle size computing means 1070 computes the particle diameter de', assuming that the particle is a sphere (a circle on the image) as shown with a broken line A' although the particle is actually an oblate as shown with a full line A in FIG. 18. The diameter de' is computed by the first particle size computing means 1070, but another device for computing a radius is not excluded from the scope of the invention.

$$d'_e = 2\sqrt{\frac{S}{\pi}} \qquad \text{[Expression 8]}$$

An error due to the position of the particle in the third axial direction may be included in the result de' computed with the above-mentioned expression. Such a point is now mentioned, referring to FIG. 19 and FIG. 20.

In FIG. 19, the camera is denoted with a reference number 1060, and a focal face of the camera is denoted with a reference numeral 1060a. In the case of FIG. 19, a middle particle A2 flows on the focal face 1060a, an upper particle A1 in the figure flows on a side far from the camera 1060 with respect to the focal face 1060a, and a lower particle A3 in the figure flows on aside close to the camera 1060 with respect to the focal face 1060a. FIG. 20 is a typical view of an image of these three particles. FIG. 19 and FIG. 20 are similar views, but are different in their view directions. FIG. 19 is a view seen from the second axial direction side (+side of y axis), and FIG. 20 is a view seen from one side of the third axis (z axis) (view of the image obtained by imaging means). Although the particle A2 flowing on the focal face 1060a is imaged as a smallest one in the image (see FIG. 20), the other two particles (the particle A1 flowing on the side far from the focal face 1060a and the particle A3 flowing on the side close to the focal face 1060a) are imaged as blurred big ones in comparison with the middle particle A2 (see FIG. 20). For this reason, the apparent diameters de' of both particles A1, A3 are computed as ones bigger than the actual ones. In order to delete such errors, it is necessary to compensate the particle diameter de' according to amount of deviation from the focal face 1060a (see reference marks Δz1 and Δz3 of FIG. 19).

Then, following means are provided in this embodiment, through which the amount of deviation Δz of the particle from the focal face 1060a is compensated.

a third axis directional position computing means 1073 (see FIG. 15, details is mentioned hereinafter), for computing the third axis directional position z of the particle based upon the computed results by the flow measuring means 1004, the flow speed computing means 1071 and the second axis directional position measuring means 1072 and the Navier-Stokes equation regarding the fluid flowed in the micro-channel 1002a, a deviation computing means 1074, for computing the amount of deviation Δz of the particle in the third axial direction with respect to the focal face 1060a of the imaging means 1006 based upon the computed result of the third axis directional position computing means 1073, a blur predicting means 1075, for predicting the degree of blur of the image of the particle (a relative rate between the apparent particle diameter de' and the actual particle diameter) based upon the computed result of the deviation computing means 1074, a second particle size computing means 1076, for compensating the apparent particle diameter de' based upon the predicted result of the blur predicting means 1075.

For easy understanding, the particle diameter dp compensated by the second particle size computing means 1076 is referred to as "compensated particle diameter".

The third axis directional position computing means 1073 and the Navier-Stokes equation are now mentioned.

An analytical solution of flowing speed of the Navier-Stokes equation in a case where the micro-channel 1002a has a rectangle section is as follows.

$$u = \frac{Q}{\frac{2D^3W}{3} + \frac{256D^4}{\pi^5} \sum_{n=1,3,5,\ldots}^{m} \left\{ \frac{1}{n^5} \cos(n\pi) \tanh\left(\frac{n\pi W}{4D}\right) \right\}} \times$$  [Expression 9]

$$\left\{ \frac{z}{2}(2D-z) - \frac{16D^2}{\pi^3} \sum_{n=1,3,5,\ldots}^{m} \frac{1}{n^3} \sin\left(\frac{n\pi}{2D}z\right) \frac{\cosh\left(\frac{n\pi}{2D}y\right)}{\cosh\left(\frac{n\pi W}{4D}\right)} \right\}$$

where

D=half of width of micro-channel in the third axial direction (see FIG. 3)

W=width of micro-channel in the second axial direction (see FIG. 3)

u=flow speed of particulate

Q=flow y=second axis directional position of the particulate z=third axis directional position of the particulate.

In this case, values of D and W are known values, a value of half of a height of the channel and a width of the channel, and the flow speed u is computed by the flow speed computing means 1071, the flow Q is computed by the flow measuring means 1004, and the position of the particle in the second axial direction is measured by the second axis directional position measuring means 1072. Then, any values are known values. Therefore, the position of the particle in the third axial direction z is obtained with the above-mentioned equation.

By doing so, a relation between the flow speed u and the third axis directional position z is obtained.

$Q$=0.028 [μl/s]

$D$=⁵⁰⁄₂=25 [μm]

$W$=200 [μm]  [Expression 6]

In a case of the above-mentioned expression, the relation between the flow speed u and the third axis directional position z ($0 \leq z \leq 25$) becomes one as shown in FIG. 21, and the third axis directional position z is computed based upon the computed result u of the flow speed computing means 1071.

Figure 25:
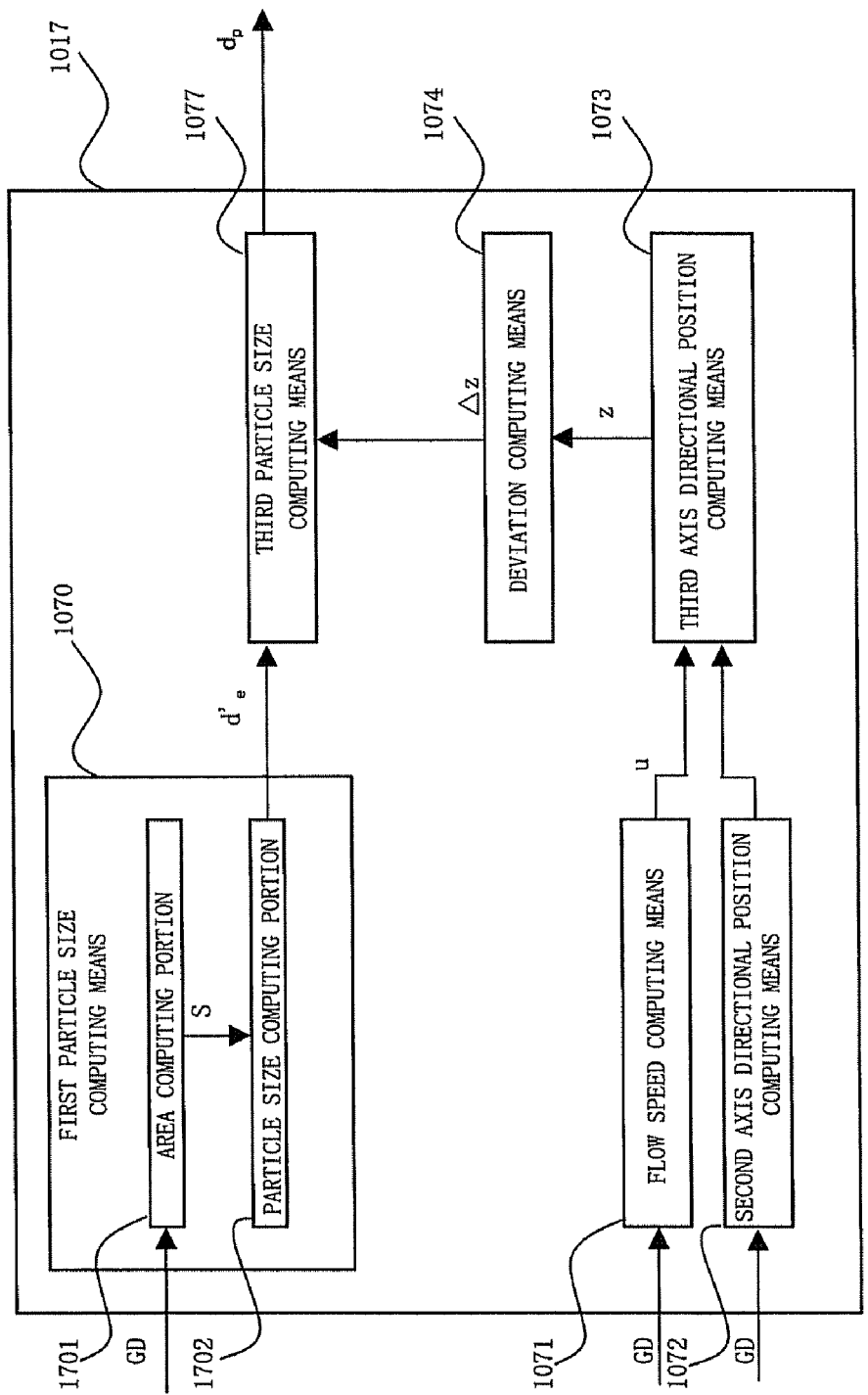
FIG. 25 is a block diagram showing the other example of a structure of an important portion (data processor) of the particle size measuring device according to the invention.

The data processor 1017 as shown in FIG. 25 may be used in place of the data processor 1007 in FIG. 15. The data processor 1017 is different from the data processor 1007 only in such a point that a third particle size computing means 1077 is used in place of the blur predicting means 1075 and the second particle size computing means 1076. The third particle size computing means 1077 computes the particle diameter dp based upon the apparent particle diameter de' and the amount of deviation Δz and the following expression.

$f(d_p, d_e', \Delta z) = 0$  [Expression 11]

where $d_e'$=apparent particle diameter

Δz=amount of deviation.

Besides, the value dp may be computed by the following expression.

$d_p = a\Delta z + b$ or $d_p = a(\Delta z)^2 + b(\Delta z) + c$  [Expression 12]

where a, b and c are constants approximately obtained from $d_e'$, Δz, and M and $d_s$ mentioned hereinafter.

Furthermore, the value dp may be computed by the following expression.

[Expression 13]

$$d_e' = \sqrt{M^2 d_p^2 + d_s^2 + \left\{\frac{MD_a \cdot \Delta z}{(s_o + \Delta z)}\right\}^2}$$  (ExA)

that is, $$d_p = \frac{1}{M} \sqrt{(d_e')^2 - d_s^2 - \left\{\frac{MD_a \cdot \Delta z}{(s_0 + \Delta z)}\right\}^2}$$

where $d_e'$=said apparent particle diameter

M=magnification of said imaging means $d_s$=airy disk diameter due to diffraction $D_a$=effective diameter of lens $s_o$=distance from main point of lens to focal face Δz=said amount of deviation.

A second term of right hand side in the above-mentioned expression A relates to the influence due to diffraction with respect of the blur of the image, and the third term of right hand side relates to the influence of the amount of deviation on the particle diameter. By solving the above-mentioned expression, it is possible to compute the value after deleting the influence due to diffraction or the amount of deviation (particle diameter dp).

The airy disk diameter ds can be obtained by the following expression.

$$d_s = \frac{1.22(1+M)\lambda}{NA}$$  [Expression 14]

where

M=magnification of said imaging means

λ=wavelength of light.

NA=number of openings of optical system.

According to the invention, based upon the image data obtained by imaging the particles from a direction through a camera, the position of the particle in its depth direction (the third axial direction) can obtained and the particle diameter can be compensated. According to the invention, it is possible to accurately measure the diameter of the particle through the device with a simple structure.

The inventors confirmed the measurement accuracy of the device according to the invention by experiments.

Experiment 1

The sample on the market, including particles (their diameters are 2 μm) therein has been measured with the particle size measuring device 1001. The distribution of the particle diameter should correspond to the Gauss distribution, but the solution result with no compensation through the second particle size computing means 1076 became a bar graph as shown in FIG. 22(*a*), and did not correspond to the Gauss distribution (broken line). On the contrary, the solution result with the compensation through the second particle size computing means 1076 became a bar graph as shown in FIG. 22(*b*), and corresponded to the Gauss distribution (broken line). That is, the inventors confirmed high measurement accuracy.

Experiment 2

The following four kinds of samples have been prepared,
fluid including polystyrene•latex particles therein each diameter of which is 2 μm
fluid including polystyrene•latex particles therein each diameter of which 5 μm
fluid including polystyrene•latex particles therein each diameter of which is 10 μm
fluid including polystyrene•latex particles therein each diameter of which is 20 μm.

Then, the particle diameter of each sample has been measured by the above-mentioned particle size measuring device 1001. The result is shown in FIG. 23, and it was found the measurement accuracy of the device was high.

FIG. 24 is a view showing a relation between a value of the measured particle diameter $d_y$ and the actual particle diameter (a value published by a manufacturer) $d_x$. Needless to say, an ideal is that the relation between $d_y$ and $d_x$ is equal to the relation $d_y = d_x$ (a straight line passing through an origin and the straight line rising in a right direction, having an inclination 45 degree). When plotting measurement result of FIG. 23, $d_y = 0.985 d_x + 0.550$ ($d_y$ corresponds to the above-mentioned value dp), and it was found that the relation is close to $d_y = d_x$, and the measurement accuracy of the device of the invention was high. In a case of no compensation in connection with the amount of deviation Δz, $d_y = 0.827 d_x + 4.240$ ($d_y$ corresponds to the above-mentioned value de'), and such a relation is widely shifted from a straight line $d_y = d_x$. From this fact, it was found that an effectiveness of the compensation of the particle diameter according to the invention was confirmed.

The apparent particle diameter de' may be bigger one than the actual one due to a phenomenon of diffraction of light. In a case where the particle diameter on the image is de, the actual particle diameter is dp, an airy disk diameter due to diffraction is ds, a magnification of an imaging optical system is M, wavelength of light is λ, and number of openings is NA, the following expression is formed. For example, the apparent particle diameter de may be ≈19 through 30 μm if M=5, λ=visible light (400 through 700 nm), and NA=0.18 although the actual particle diameter dp is 2 μm. In other words, the apparent particle diameter is a convolution of the actual particle diameter and PSF, and the particle diameter computed by the first particle size computing means 1070 from the image data GD becomes a very big value than the actual particle diameter dp.

$$d_e = \sqrt{M^2 d_p^2 + d_s^2}$$
$$d_s = \frac{1.22(1+M)\lambda}{NA}$$

[Expression 15]

Preferably, fourth particle size computing means (not shown) is provided with the data processor 1007, and a deconvolution procedure is executed in order to compensate the error due to a phenomenon of diffraction of light.

The present invention has been explained on the basis of the example embodiments discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. A particle measuring device for measuring particles based upon image data, comprising:
   a micro-channel wherein fluid mixing particles therein flows, forming laminar flow;
   imaging means, for imaging said particles flowed in said micro-channel from a direction almost orthogonal to a fluid flow direction;
   particle speed measuring means, for measuring speed of said particle flowed based upon said image data obtained by imaging through said imaging means;
   particle number counting means, for counting number of said particles flowed within a predetermined time based upon said image data obtained by imaging through said imaging means;
   particle size measuring means, for measuring diameter of said particle flowed based upon said image data obtained by imaging through said imaging means; and
   data associating means, for associating measurement values measured by respective measuring means and time with each other based upon time when measuring through said respective measuring means and controlling thus associated;
   said particle number counting means, further comprising:
   a differential image forming portion, for forming a differential image from two stationary images obtained by imaging through said imaging means;
   a relating portion, for relating said particle to a position to which said particle moved;
   a particle number counting portion, for counting number of said particles based upon data from said relating portion;
   a particle position predicting portion, for predicting a position of said particle in a next stationary image from speed of said respective particles obtained through said particle speed measuring means;
   a particle movement predicting portion, for predicting movement of said particle, such as overlapping of particles and passing of particles in said next stationary image, based upon data of said particle position predicting portion; and a particle number compensating portion, for compensating measurement data of said particle number counting portion based upon data from said particle movement predicting portion and obtaining number of particles which actually exist in said next stationary image.

2. The particle measuring device according to claim 1, wherein said particle speed measuring means has
a movement distance computing portion, for computing movement distance of each particle by executing imaging processing on two or more stationary images obtained by imaging through said imaging means, and
a particle speed computing portion, for computing the speed by dividing said computed movement distance by imaging interval.

3. The particle measuring device according to claim 1, wherein said particle size measuring means has a first particle size computing means, for computing a diameter of said particle on the image based upon said image data obtained by imaging through said imaging means.

4. The particle measuring device according to claim 3, wherein said particle size measuring means has a particle size compensating portion, for compensating a computed result of said first particle size computing means based upon amount of deviation of said particle with respect to a focal face of said imaging means.

5. The particle measuring device according to claim 1, wherein said fluid is one of liquid, gas, two-phase fluid of liquid-gas, two-phase fluid of liquid-solid, two-phase fluid of gas-solid, and multi-phase fluid of liquid-gas-solid.

6. A particle size measuring device for measuring diameter of particles mixed in fluid, comprising:
a micro-channel for flowing fluid including particles therein in a first axial direction;
imaging means, for imaging said particles flowed in said micro channel, said imaging means being located so as to image a third axial direction almost orthogonal to said first axial direction;
flow measuring means, for measuring flow of fluid flowed in said micro-channel;
a first particle size computing means, for computing an apparent particle diameter on an image based upon image data obtained by imaging through said imaging means;
flow speed computing means, for computing flow speed of said particle based upon said image data;
second axis directional position measuring means, for measuring a position of said particle in a second axial direction almost orthogonal to said first axial direction and said third axial direction from said image data;
third axis directional position computing means, for computing a position of said particle in said third axial direction based upon computed results through said flow measuring means, said flow speed computing means and said second axis directional position measuring means and a Navier-Stokes equation regarding fluid flowed in said micro-channel;
deviation computing means, for computing amount of deviation of said particle in said third axial direction with respect to said focal face of said imaging means based upon computed result of said third axis directional position computing means;
blur predicting means, for predicting degree of blur of an image of said particle based upon computed result of said deviation computing means; and
second particle size computing means, for compensating said apparent diameter of said particle based upon predicted result of said blur predicting means.

7. A particle size measuring device for measuring diameter of particles mixed in fluid, comprising:
a micro-channel for flowing fluid including particles therein in a first axial direction;
imaging means, for imaging said particles flowed in said micro channel, said imaging means being located so as to image a third axial direction almost orthogonal to said first axial direction;
flow measuring means, for measuring flow of fluid flowed in said micro-channel;
a first particle size computing means, for computing apparent diameter of said particle on an image based upon image data obtained by imaging through said imaging means;
flow speed computing means, for computing flow speed of said particle based upon said image data;
a second axis directional position measuring means, for measuring a position of said particle in a second axial direction almost orthogonal to said first axial direction and said third axial direction from said image data;
third axis directional position computing means, for computing a position of said particle in said third axial direction based upon computed results through said flow measuring means, said flow speed computing means and said second axis directional position measuring means and the Navier-Stokes equation regarding fluid flowed in said micro-channel;
deviation computing means, for computing amount of deviation of said particle in said third axial direction with respect to said focal face of said imaging means based upon computed result of said third axis directional position computing means; and
third particle size computing means, for computing particle diameter dp from said apparent diameter of said particle, said amount of deviation and the following expression $$f(d_p, d_e', \Delta z) = 0$$

where de'=said apparent diameter of said particle
$\Delta z$=said amount of deviation.

8. The particle size measuring device according to claim 7 wherein said expression is the following one:

$$d_e' = \sqrt{M^2 d_p^2 + d_s^2 + \left\{\frac{MD_a \cdot \Delta z}{s_a + \Delta z}\right\}^2}$$

where
de'=said apparent particle diameter
M=magnification of said imaging means
ds=airy disk diameter due to diffraction
Da=effective diameter of lens
so=distance from main point of lens to focal face
$\Delta z$=said amount of deviation.

9. The particle size measuring device according to claim 7, wherein said first particle size computing means is comprised of an area computing portion, for computing area S of said particle based upon said image data, and a particle size computing portion, for computing said apparent particle diameter de' based upon said area S computed by said area computing portion and the following expression.

$$d'_e = 2\sqrt{\frac{S}{\pi}}$$

10. The particle size measuring device according to claim 7, wherein said micro-channel has a form so as to flow said fluid, forming laminar flow.

11. The particle size measuring device according to claim 7, wherein said flow measuring means is comprised of a storage container for storing fluid flowed out of said micro-channel, a weight measuring portion for measuring weight of fluid stored in said storage container, and a flow computing portion for computing flow based upon a result measured by said weight measuring portion and time data.

12. The particle size measuring device according to claim 7, further comprising fourth particle size computing means, for compensating errors due to a phenomenon of diffraction of light by executing deconvolution procedure.

13. The particle size measuring device according to claim 7, wherein said fluid is one of liquid, gas, two-phase fluid of liquid-gas, two-phase fluid of liquid-solid, two phase fluid of gas-solid, and multi-phase fluid of liquid-gas-solid.

* * * * *